United States Patent [19]
Farina et al.

[11] Patent Number: 6,025,390
[45] Date of Patent: Feb. 15, 2000

[54] HETEROAROMATIC PENTADIENOIC ACID DERIVATIVES USEFUL AS INHIBITORS OF BONE RESORPTION

[75] Inventors: Carlo Farina, Milan; Stefania Gagliardi, Como, both of Italy; Guy Marguerite Marie Gérard Nadler, Rennes; Michel Jean Roger Martin, St Gregoire, both of France

[73] Assignees: SmithKline Beecham SpA, Milan; SmithKline Beecham Farmaceutici, Rome, both of Italy

[21] Appl. No.: 09/214,689

[22] PCT Filed: Jul. 7, 1997

[86] PCT No.: PCT/EP97/03709

§ 371 Date: Jun. 23, 1999

§ 102(e) Date: Jun. 23, 1999

[87] PCT Pub. No.: WO98/01436

PCT Pub. Date: Jan. 15, 1998

[30] Foreign Application Priority Data

Jul. 9, 1996 [GB] United Kingdom ............ 9614347

[51] Int. Cl.[7] .................. A61K 31/34; A61K 31/38; A61K 31/445; C07D 215/00; C07D 401/00
[52] U.S. Cl. .................. 514/469; 514/443; 514/320; 514/324; 514/311; 549/471; 549/467; 549/58; 546/196; 546/202; 546/165; 546/174; 546/175
[58] Field of Search ................ 514/469, 443, 514/320, 324, 311; 549/471, 467, 58; 546/196, 202, 165, 174, 175

[56] References Cited

U.S. PATENT DOCUMENTS

| | | | |
|---|---|---|---|
| 5,731,352 | 3/1998 | Lesieur et al. | 514/630 |
| 5,792,763 | 8/1998 | Fritz et al. | 514/228.2 |
| 5,807,889 | 9/1998 | Perregaard | 514/469 |
| 5,856,490 | 1/1999 | Teng et al. | 546/165 |
| 5,856,503 | 1/1999 | Aebi et al. | 548/207 |
| 5,856,529 | 1/1999 | Catt et al. | 549/469 |
| 5,858,995 | 1/1999 | Kawai et al. | 514/100 |
| 5,863,936 | 1/1999 | Gaeta et al. | 514/443 |
| 5,935,972 | 8/1999 | Naylor et al. | 514/320 |
| 5,952,347 | 9/1999 | Arison et al. | 514/311 |

FOREIGN PATENT DOCUMENTS

| | | |
|---|---|---|
| 0 189 936 | 8/1986 | European Pat. Off. . |
| 0 449 196 | 10/1991 | European Pat. Off. . |
| WO 92/14709 | 9/1992 | WIPO . |
| WO 96/21644 | 7/1996 | WIPO . |

OTHER PUBLICATIONS

Popa, et al., "Synthesis of abscisic acid analogs with anti-transpirant properties", *Chemical Abstracts,* 108 No. 25, p. 201, column 2 (1988).

*Primary Examiner*—Deborah C. Lambkin
*Attorney, Agent, or Firm*—Soma G. Simon; William T. King; Charles M. Kinzig

[57] ABSTRACT

A compound of formula (I) or a salt thereof, or a solvate thereof,

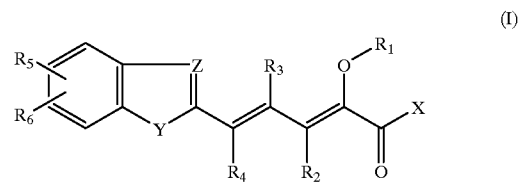

wherein: $R_1$ represents an alkyl group or a substituted or unsubstituted aryl group; $R_2$, $R_3$ and $R_4$ each independently represent hydrogen, alkyl, aryl or substituted aryl; $R_5$ and $R_6$ each independently represent hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_5$ and $R_6$ together represent methylenedioxy, carbonyldioxy or carbonyldiamino; X represents a hydroxy or an alkoxy group wherein the alkyl group may be substituted or unsubstituted or X represents a group $NR_SR_t$ wherein $R_S$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_S$ and $R_t$ together with the nitrogen to which they are attached form a heterocyclic group; and Y represents O or S and Z represents CH, CH=CH or N; or Y represents $NR_7$ wherein $R_7$ represents hydrogen, hydroxy, alkanoyl, alkyl, aminoalkyl, hydroxyalkyl, carboxyalkyl, carbalkoxyalkyl, carbamoyl or aminosulphonyl and Z represents CH=CH or N; a pharmaceutical composition containing such a compound, a process for preparing such a compound and the use of such a compound in medicine.

10 Claims, No Drawings

HETEROAROMATIC PENTADIENOIC ACID DERIVATIVES USEFUL AS INHIBITORS OF BONE RESORPTION

This appln is a 371 of PCT/EP97/03709 Jul. 7, 1997.

This invention relates to certain novel compounds, to a process for preparing such compounds, to pharmaceutical compositions containing such compounds and to the use of such compounds and compositions in medicine.

Co-pending International Application, application number PCT/EP96/00157 discloses certain indole derivatives which are indicated to reduce bone resorption by inhibiting osteoclast $H^+$-ATPase.

Diseases associated with loss of bone mass are known to be caused by over activity of osteoclast cells. It is also known that certain compounds, usually related to bafilomycin, are useful for treating such diseases: For example International Patent Application, publication number WO 91/06296 discloses certain bafilomycin macrolides for the treatment of bone affecting diseases.

However, bafilomycin derivatives are not selective for osteoclasts in humans. The use of these compounds is therefore associated with unacceptable toxicity due to generalised blockade of other essential v-ATPases. Indeed, to date there is no known treatment which is selective for the human osteoclasts.

The search for a successful treatment for diseases associated with loss of bone mass in humans is further complicated in that the nature of the therapeutic target for the selective inhibition of the osteoclasts is controversial. Thus Baron et al (International Patent Application publication number WO 93/01280) indicate that a specific vacuolar ATPase (V-ATPase) has been identified in osteoclasts as a potential therapeutic target. However, the Baron work was carried out in chickens and Hall et al (Bone and Mineral 27, 1994, 159–166), in a study relating to mammals, conclude that in contrast to avian osteoclast V-ATPase, mammalian osteoclast V-ATPase is pharmacologically similar to the v-ATPase in other cells and, therefore, it is unlikely to be a good therapeutic target.

We have now found a group of compounds which are selective for mammalian osteoclasts, acting to selectively inhibit their bone resorbing activity. These compounds are therefore considered to be particularly useful for the treatment and/or phophylaxis of diseases associated with loss of bone mass, such as osteoporosis and related osteopenic diseases, Paget's disease, hyperparathyroidism and related and related diseases. These compounds are also considered to possess anti-tumour activity, antiviral activity (for example against Semliki Forest, Vesicular Stomatitis, New castle Disease, Influenza A and B, HIV viruses), antiulcer activity (for example the compounds may be useful for the treatment of chronic gastritis and peptic ulcer induced by *Helicobacter pylori*), immunosupressant activity, antilipidemic activity, antiatheroselerotic activity and to be useful for the treatment of AIDs and Alzheimer's disease. In a further aspect, these compounds are also considered useful in inhibiting angiogenesis, i.e. the formation of new blood vessels which is observed in various types of pathological conditions (angiogenic diseases) such a rheumatoid arthritis, diabetic retinopathy, psoriasis and solid tumours.

Accordingly, the present invention provides a compound of formula (I):

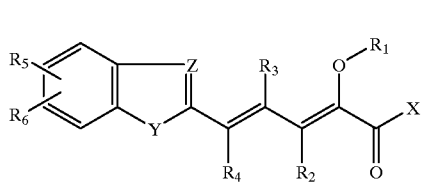

or a salt thereof, or a solvate thereof, wherein:

$R_1$ represents an alkyl group or a substituted or unsubstituted aryl group;

$R_2$, $R_3$ and $R_4$ each independently represent hydrogen, alkyl, aryl or substituted aryl;

$R_5$ and $R_6$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_5$ and $R_6$ together represent methylenedioxy, carbonyldioxy or carbonyldiamino;

X represents a hydroxy or an alkoxy group wherein the alkyl group may be substituted or unsubstituted or X represents a group $NR_SR_t$ wherein $R_S$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclylalkyl group, or $R_S$ and $R_t$ together with the nitrogen to which they are attached form a heterocyclic group; and Y represents O or S and Z represents CH, CH=CH or N; or Y represents $NR_7$ wherein $R_7$ represents hydrogen, hydroxy, alkanoyl, alkyl, aminoalkyl, hydroxyalkyl, carboxyalkyl, carbalkoxyalkyl, carbamoyl or aminosulphonyl and Z represents CH=CH or N.

Suitably, Y represents O or S and Z represents CH, CH=CH or N, especially CH or CH=CH.

In one aspect $R_1$ represents alkyl, alkoxyalkyl or substituted or unsubstituted phenyl.

Suitably, $R_1$ represents a $C_{1-4}$-alkyl group, for example methyl or ethyl.

Preferably, $R_1$ represents methyl.

In one aspect, $R_2$, $R_3$ and $R_4$ each independently represent hydrogen, alkyl or phenyl.

An example of $R_2$ is hydrogen.
An example of $R_3$ is hydrogen.
An example of $R_4$ is hydrogen.

Suitably, $R_5$ and $R_6$ each independently represents hydrogen or a halo atom.

When $R_5$ or $R_6$ represents halo, said halo group is suitably a fluoro or chloro group.

An example of a halo is chloro.

Suitable positions for substitution for $R_5$ or $R_6$ are the 4, 5, 6 or 7 position, favourably the 5 or 6 position.

When X represents an alkoxy group, the alkyl group thereof is preferably an unsubstituted alkyl group.

An example of an alkoxy group represented by X is a methoxy group.

Suitably, X represents the above defined group $N R_S R_t$.

When $R_S$ or $R_t$ represent alkyl or substituted alkyl, suitable alkyl groups are $C_{1-6}$ alkyl groups, for example $C_1$, $C_2$, $C_3$, $C_4$ and $C_5$ alkyl groups, favourably ethyl, propyl or butyl.

When $R_S$ or $R_t$ represent substituted alkyl, favoured groups are 2-(dialkylamino)ethyl or 3-(dialkylamino)propyl or 4-(dialkylamino)butyl or heterocyclylmethyl or heterocyclylethyl or heterocyclylpropyl groups, especially 3-(dialkylamino)propyl groups. An example of a 3-(dialkylamino)propyl group is a 3-(diethylamino)propyl group.

When $R_S$ or $R_t$ represent alkenyl or substituted alkenyl, suitable alkenyl groups are $C_{2-6}$ alkenyl groups, for example at $C_5$ alkenyl group.

When $R_S$ or $R_t$ represent aryl or substituted aryl, suitable aryl groups are phenyl groups.

In one aspect, $R_S$ and $R_t$ together represent a heterocyclic group.

In one favoured aspect $R_t$ is hydrogen.

A particular 6 membered, saturated heterocyclic group is a group of formula (H1):

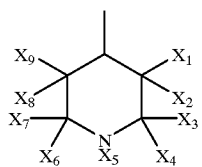

(H1)

wherein $X_1$, $X_2$, $X_3$, $X_4$, $X_5$, $X_6$, $X_7$ and $X_8$ are each independently selected from hydrogen, hydroxy, ($C_1$–$C_6$), alkyl cycloalkyl (spirocondensed), mono or poly hydroxyalkyl, alkoxyalkyl, hydroxy-alkoxyalkyl, alkanoyl, alkoxycarbonyl, aminoalkyl (optionally alkylated or acylated at nitrogen);

or one of $X_4$ with $X_6$ and $X_2$ with $X_8$ represents a $C_{2-4}$ alkylene chain and the remaining variables $X_1$, $X_3$, $X_7$ and $X_7$ each independently represent hydrogen, hydroxy, lower alkyl ($C_1$–$C_6$), cycloalkyl (spirocondensed), mono or poly hydroxyalkyl, alkoxyalkyl, hydroxy-alkoxyalkyl, alkanoyl, alkoxycarbonyl, aminoalkyl (optionally alkylated or acylated at nitrogen); and $X_5$ represents hydrogen or lower alkyl, mono or polyhydroxyalkyl, mono or diaminoalkyl, aminocarbonyl, alkyl, carboxyalkyl, carbalkoxyalkyl, aryl, heterocyclyl, acyl, carbamoyl, alkylamino(cyanimidoyl), aminoalkanoyl, hydroxyalkanoyl.

Suitably, $X_1$, $X_2$, $X_8$ and $X_9$ each represent hydrogen.

Suitably, $X_3$, and $X_4$ each independently represent hydrogen or alkyl, especially alkyl.

Suitably, $X_6$ and $X_7$ each independently represent hydrogen or alkyl.

Suitably, $X_5$ represents alkyl

In one preferred aspect $X_3$, $X_4$, $X_6$ and $X_7$ each independently represent alkyl, especially methyl and X1, $X_2$, $X_8$ and $X_9$ each represent hydrogen.

Particular examples of the invention are the compounds of example numbers; 3, 5, 8, 9 and 12.

As used herein, the term "alkyl" includes straight or branched chain alkyl groups having from 1 to 12, suitably 1 to 6, preferably 1 to 4, carbon atoms, such as methyl, ethyl, n- and iso- propyl and n- iso-, tert-butyl and pentyl groups, and also includes such alkyl groups when forming part of other groups such as alkoxy or alkanoyl groups.

Suitable optional substituents for any alkyl group include hydroxy, alkoxy; a group of formula $NR_uR_v$ wherein $R_u$ and $R_v$ each independently represent hydrogen, optionally substituted alkyl, optionally substituted cycloalkyl, optionally substituted aryl, optionally substituted arylalkyl, optionally substituted heterocyclyl, optionally substituted heterocyclylalkyl, carboxy, carboxyalkyl, or alkoxycarbonyl, nitro, $R_u$ and $R_v$ together together with the nitrogen to which they are attached form an optionally substituted heterocyclic ring; carboxy; alkoxycarbonyl; alkoxycarbonylalkyl; alkylcarbonyloxy; alkylcarbonyl; mono- and di-alkylphosphoate; optionally substituted aryl; and optionally substituted heterocyclyl.

A preferred alkyl substituent is $NR_uR_v$, wherein $R_u$ and $R_v$ each independently represent hydrogen, optionally substituted aryl, optionally substituted arylalkyl, optionally substituted heterocyclyl, optionally substituted heterocyclylalkyl or $R_u$ and $R_v$ together together with the nitrogen to which they are attached form an optionally substituted heterocyclic ring.

As used herein, the term "alkenyl" includes straight or branched chain alkenyl groups having from 2 to 12, suitably 2 to 6 carbon and also includes such groups when forming part of other groups, an example is a butenyl group, such as a 2-butenyl group.

Suitable optional substituents for any alkenyl group includes the alkyl substituents mentioned above.

As used herein, the term "aryl" includes phenyl and naphthyl, especially phenyl.

Suitable optional substituents for any aryl group include up to 5 substituents, suitably up to 3 substituents, selected form alkyl, substituted alkyl, alkoxy, hydroxy, halogen, trifluoromethyl, acetyl, cyano, nitro, amino, mono- and di-alkylamino and alkylcarbonylamino.

Preferred optional substituents for any aryl group are selected from isobutyl, hydroxy, methoxy, phenoxy, diethylaminoethoxy, pyrrolidinoethyoxy, carboxymethoxy, pyridyloxy, fluoro, chloro, amino, dimethylamino, aminomethyl, morpholino, bis(carbethoxy)hydroxymethyl, Suitable arylalkyl groups include aryl-$C_{1-3}$-alkyl groups such as phenylethyl and benzyl groups, especially benzyl.

Preferably, substituted aralkyl groups are substituted in the aryl moiety.

As used herein, the terms "heterocyclyl" or "heterocyclic" include saturated or unsaturated single or fused, including spiro, ring heterocyclic groups, each ring having 4 to 11 ring atoms, especially 5 to 8, preferably 5, 6 or 7 which ring atoms include 1, 2 or 3 heteroatoms selected from O, S, or N.

Suitable heterocyclic groups include single ring saturated heterocyclic groups, single ring unsaturated heterocyclic groups, fused ring heterocyclic groups.

Fused ring heterocyclic groups include spiro heterocyclic groups.

Suitable single ring unsaturated heterocyclic groups comprise 5-, 6-, or 7-membered rings.

Suitable 5-membered single ring unsaturated heterocyclic groups are furanyl, thienyl, pyrrolyl, pyrazolyl, imidazolyl, triazolyl, tetrazolyl, oxazolyl, isoxazolyl, furazanyl, thiazolyl and isothiazolyl groups; or partially saturated derivatives thereof, such as 4,5-dihydro-1,3-thiazol-2-yl, 1H-imidazolinyl, pyrrolinyl, pyrazolinyl, oxazolinyl, isoxazolinyl, thiazolinyl groups.

Suitable 6-membered single ring unsaturated heterocyclic groups are pyridyl, pyrimidinyl, pyridazinyl, pyrazinyl, triazinyl, tetrazinyl, 1,2- or 1,3- or 1,4-oxazinyl, 1,2- or 1,3- or 1,4-thiazinyl and pyranyl groups, or partially saturated derivatives thereof such as 1,2- or 1,3- or 1,4-dihydrooxazinyl, 1,4-dihydropyridyl, dihydropyridazinyl, dihydropyrazinyl or dihydropyrimidinyl.

Suitable 7-membered single ring unsaturated heterocyclic groups are azepinyl, oxepinyl, diazepinyl, thiazepinyl, oxazepinyl or partially saturated derivatives thereof.

Suitable, single ring saturated heterocyclic groups comprise 5-, 6- or 7-membered rings.

Suitable 5-membered single ring saturated heterocyclic groups are pyrrolidnyl, imidazolidinyl, pyrazolidinyl, oxazolidinyl, isoxazolidinyl and terahydrofuranyl groups.

Suitable 6-membered single ring saturated heterocyclic groups are piperidinyl, piperazinyl, tetrahydropyranyl, 1,3-dioxacyclohexyl, tetrahydro-1,4-thiazinyl, morpholinyl and morpholino groups.

Suitable 7-membered single ring saturated heterocyclic groups are hexamethyleniminyl, oxepinyl and thiepanyl.

Suitable fused ring heterocyclic groups include fused saturated rings, fused unsaturated rings and saturated rings fused to unsaturated rings.

Suitable groups having fused saturated rings are quinuclidyl, 8-azabicyclo[3.2.1]octyl, 9-azabicyclo[3.3.1]nonyl, 1-azabicyclo[3.3.3]undecyl, 1,9-diazabicyclo[3.3.1]nonyl and 1,5-diazabicyclo[3.3.1]nonyl groups.

Suitable groups having fused unsaturated rings are pyrazo[3.4-d]pyrimidinyl, 1,2,5-thiadiazolo[3,4-b]pyridyl, isoxazolo[4,5-b]pyridyl, thiazolo[4,5-b]pyridyl, oxazolo[4,5-d]pyrimidinyl, 7H-purin-2-yl, quinolyl, isoquinolyl, benzo[b]thienyl, benzoduranyl, isobenzofuranyl, benzoxazolyl, benzothiazolyl, indolizinyl, indolyl, isoindolyl, indazolyl, phthalazinyl, naphthyridinyl, quinoxalinyl, quinazolinyl, cinnolinyl, pteridinyl and β-carbolinyl groups.

Suitable groups having saturated rings fused to unsaturated rings includes groups which are fused to benzene rings such as tetrahydroquinoloyl, 4H-quinolizinyl, tetrahydroisoquinolyl, dihydrobenzofuryl, chromenyl, chromanyl, isochromanyl, indolinyl and iosoindolinyl groups.

Suitable spiro heterocyclic groups include oxaspiro[4.5]decyl, azaspiro[4.5]decyl, 1,2,4-triazaspiro[5.5]undecyl, 1,4-dioxa-9-azaspiro[4.7]dodecyl and 1-azaspiro[5.5]undecyl.

Suitable optional substituents for any heterocyclyl or heterocyclic group include up to 5 substituents, suitably up to 3 substituents, selected from alkyl, substituted alkyl, alkoxy, hydroxy, halo, amino, mono- or di-alkyl amino, alkoxycarbonyl, hydroxyalkyl, alkoxyalkyl, hydroxyalkoxyalkyl, alkoxyalkyloxyalkyl, aryl, aryloxy and heterocylclyl.

Preferred optional substituents for any heterocyclyl or heterocyclic group are selected from isobutyl, hydroxy, methoxy, phenoxy, diethylaminoethoxy, pyrrolidinoethoxy, carboxymethoxy, pyridyloxy, fluoro, chloro, amino, dimethylamino, aminomethyl, morpholino, bis(carbethoxy) hydroxymethyl.

For the avoidance of doubt a reference herein to "heterocylic" includes a reference to "heterocyclyl".

As used herein, the term "halo" includes fluoro, chloro and bromo, suitably fluoro and chloro, favourably chloro.

Certain of the carbon atoms of the compounds of formula (I)-such as those compounds wherein $R_1$–$R_4$ contains chiral alkyl chains are chiral carbon atoms and may therefore provide stereoisomers of the compound of formula (I). The invention extends to all stereoisomeric forms of the compounds of formula (I) including enantiomers and mixtures thereof, including racemates. The different stereoisomeric forms may be separated or resolved one from the other by conventional methods or any given isomer may be obtained by conventional stereospecific or asymmetric syntheses.

The compounds of formula (I) also possess two double bonds and hence can exist in one or more geometric isomers. The invention extend to all such isomeric forms of the compounds of formula (I) including mixtures thereof. The different isomeric forms may be separated one from the other by conventional methods or any given isomer may be obtained by conventional synthetic methods. Suitable salts of the compounds of the formula (I) are pharmaceutically acceptable salts.

Suitable pharmaceutically acceptable salts include acid addition salts and salts of carboxy groups.

Suitable pharmaceutically acceptable acid addition salts include salts with inorganic acids such, for example, as hydrochloric acid, hydrobromic acid, orthophosphoric acid or sulphuric acid, or with organic acids such, for example as methanesulphonic acid, toluenesulphonic acid, acetic acid, propionic acid, lactic acid, citric acid, fumaric acid, malic acid, succinic acid, salicylic acid, maleic acid or acetylsalicylic acid.

Suitable pharmaceutically acceptable salts of carboxy groups include metal salts, such as for example aluminium, alkali metal salts such as sodium or potassium and lithium, alkaline earth metal salts such as calcium or magnesium and ammonium or substituted ammonium salts, for example those with $C_{1-6}$ alkylamines such as triethylamine, hydroxy-$C_{1-6}$ alkylamines such as 2-hydroxyethylamine, bis-(2-hyroxyethyl)-amine or tri-(2-hydroxyethyl)-amine, cycloalkylamines such as dicyclohexylamine, or with procaine, 1,4-dibenzylpiperidine, N-benzyl-β-phenethylamine, dehydroabietylamine, N,N'-bisdehydroabietylamine, glucamine, N-methylglucamine or bases of the pyridine type such as pyridine, collidine or quinoline.

Suitable solvates of the compounds of the formula (I) are pharmaceutically acceptable solvates, such as hydrates.

The salts and/or solvates of the compounds of the formula (I) which are not pharmaceutically acceptable may be useful as intermediates in the preparation of pharmaceutically acceptable salts and/or solvates of compounds of formula (I) or the compounds of the formula (I) themselves, and as such form another aspect of the present invention.

A compound of formula (I) or a salt thereof or a solvate thereof, may be prepared: by reacting a compound of formula (II):

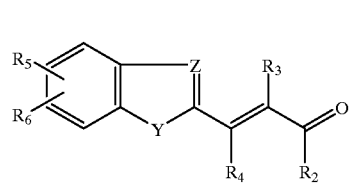

(II)

wherein $R_2$, $R_3$, $R_4$, $R_5$, $R_6$, Y and Z are as defined in relation to formula (I), with a reagent capable of converting a moiety of formula

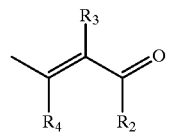

into a moiety of formula (a);

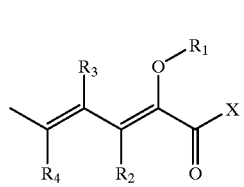

(a)

wherein $R_1$, $R_2$, $R_3$, $R_4$ and X are as defined in relation to formula (I); and thereafter, as necessary, carrying out one or more of the following reactions:

(i) converting one compound of formula (I) into another compound of formula (I);
(ii) removing any protecting group;
(iii) preparing a salt or a solvate of the compound so formed.

A suitable reagent capable of converting a moiety of the above defined formula

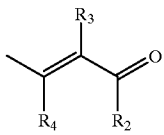

into a moiety of the above defined formula (a), includes conventional reagents used to convert C=O bonds into carbon carbon double bonds, such a Wittig or Horner-Emmons reagents, for example a compound of formula (III):

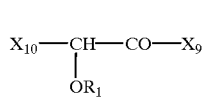

(III)

wherein $R_1$ is a defined in relation to the compounds of formula (I), $X_9$ represents X a defined in relation to formula (I) or a group convertible thereto and $X_{10}$ represents a moiety $(R_8O)_2P(O)$— wherein $R_8$ is $C_{1-4}$ alkyl, especially ethyl, or $X_{10}$ is a group $Ph_3P$—.

The reaction between the compounds of formula (II) and the reagent capable of converting the group of formula

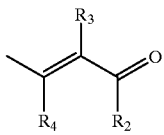

into the moiety of formula (a), may be carried out under the appropriate conventional conditions depending upon the particular reagent chosen, for example:

When the reagent is a compound of formula (III) wherein $X_{10}$ is a moiety $(R_8O)_2P(O)$—, then the reaction is carried out under conventional Horner-Emmons conditions, using any suitable, aprotic solvent for example an aromatic hydrocarbon such as benzene, toluene or xylene, DMF, DMSO, chloroform, preferably, dichloromethane, dioxane, THF, acetonitrile, N-methylpyrrolidone, and the like or mixtures thereof, preferably an anhydrous solvent, at a temperature providing a suitable rate of formation of the required product, conveniently at ambient temperature or at an elevated temperature, such as a temperature in the range of from 30° C. to 120° C., for examples 90° C.; preferably the reaction is conducted in the presence of a base.

Suitable bases for use in the last above mentioned reaction include organic base, such as butyl lithium, lithium diisopropylamide (LDA), N,N-diisopropylethylamine, 1,5-diazabicyclo[4.3.0]-5-nonene (DBN), preferably, 1,5-diazabicyclo[5.4.0]-5-undecene (DBU), 1,5-diazabicyclo[2.2.2]octane (DABCO), and inorganic bases, such as sodium hydride; and generally the reaction is carried out in an inert atmosphere such as nitrogen.

When the reagent is a compound of formula (III) wherein $X_{10}$ is a moiety $Ph_3P$—, then the reaction is carried out under conventional Wittig conditions. Usually, the reaction is carried out in the presence of a base, in any suitable aprotic solvent. Suitable bases are organic bases such as triethylamine, trimethylamine, N,N-diisopropylethylamine (DIPEA), pyridine, N,N-dimethylaniline, N-methylmorpholine, 1,5-diazabicyclo[4.3.0]-5- nonene (DBN), 1,5-diazabicyclo[5.4.0]-5-undecene (DBU), 1,5-diazabicyclo[2.2.2]octane (DABCO) and inorganic bases such as sodium hydride, caesium carbonate, potassium carbonate, preferably sodium hydride. Suitable solvents are conventional solvents for use in this type of reaction, such as aromatic hydrocarbons such as benzene, toluene or xylene or the like; DMF, DMSO, chloroform, dioxane, dichloromethane, THF, ethyl acetate, acetonitrile, N-methylpyrrolidone or mixtures thereof, preferably dichloromethane. This reaction is carried out as any temperature providing a suitable rate of formation of the required product, conveniently at ambient temperature or at an elevated temperature, such as a temperature in the range of from −20° C. to 140° C., preferably in the range of from about room temperature to the reflux temperature of the solvent.

Suitably, in the compound of formula (III), $X_9$ represents X when a hydroxy or alkoxy group in which the alkyl group may be substituted or unsubstituted; the compound of formula (I) prepared therefrom is then suitably converted to further compounds of formula (I) using methods described below.

A compound of formula (II) may be prepared according to the reaction sequences shown in Schemes (Ia–c) below

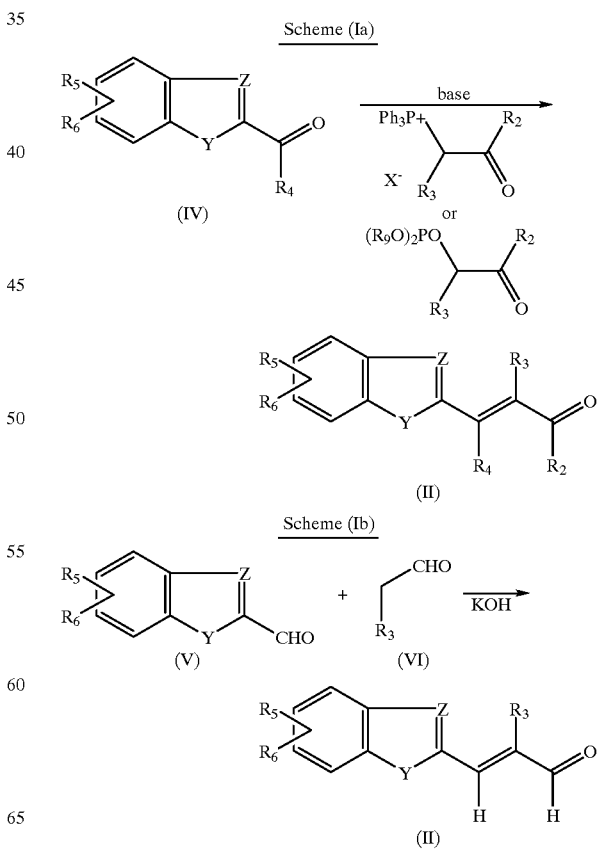

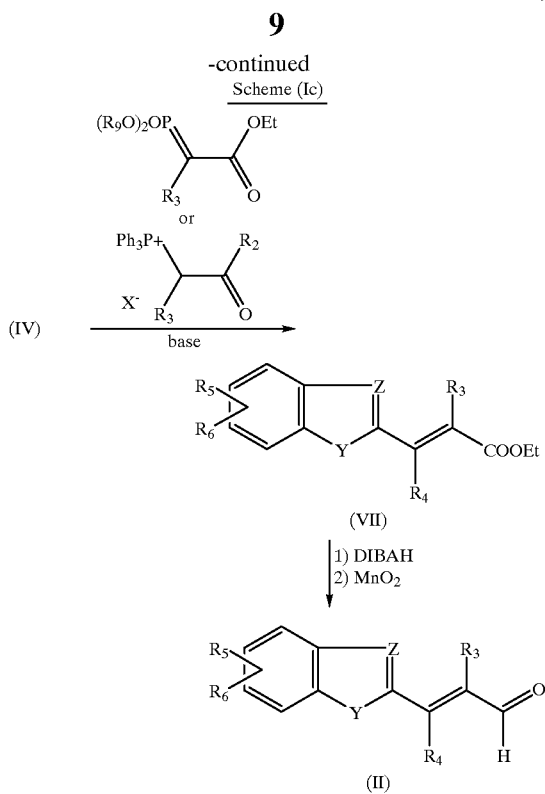

wherein, subject to any qualification mentioned below $R_2$, $R_3$, $R_4$, $R_{5,\ R6}$, X, Y and Z are as defined in relation to the compounds of formula (I).

Compounds of formula (II) may be prepared by the Wittig reaction of keto derivatives of formula (IV) with an appropriate phosphonium salt or by reaction of keto derivative (IV) with an appropriate Horner Emmons reagent. Respective reaction conditions are the appropriate conventional conditions, for example for the Wittig reaction those described in "The Wittig Reaction", R. Adams Ed., Vol. 14, p. 270 (1965) or in Angew. Chem. Int. Ed. Engl., 4, 645 (1965) and for the Horner Emmons reaction those reported, in Tetrahedron Lett. 1981, 461; Can. J. Chem., 55, 562 (1997); J. Am. Chem. Soc., 102, 1390 (1980); J. Org. Chem., 44, 719 (1979); Syntheses, 1982, 391; and Tetrahedron Lett. 1982, 2183.

When $R_2$ is other then —H, e.g., alkyl, a compound of formula (II) is obtained directly from a compound of formula (IV) by Wittig or Horner-Emmons reaction with the appropriate phosphonium salts or phosphonates according to Scheme (Ia).

The reaction of compounds of formula (IV) with the above mentioned phosphonium salts are carried out in the presence of a base in any suitable solvent. Suitable bases include organic bases, such a triethylamine, trimethylamine, N,N-diisopropylethylamine (DIPEA), pyridine, N,N-dimethylaniline, N-methylmorpholine, 1,5-diazabicyclo [4.3.09-5-nonene (DBN), 1,5-diazabicyclo[5.4.0]-5-undecene (DBU), 1,5-diazabicyclo[2.2.2]octane (DABCO) and inorganic bases, such as sodium hydride, caesium carbonate, potassium carbonate. Suitable solvents include conventionally used solvents, for example aromatic hydrocarbons such as benzene, toluene or xylene or the like; DMF, DMSO, chloroform, dioxane, dichloromethane, THF, ethyl acetate, acetonitrile, N-methylpyrrolidone and the like or mixtures thereof. Preferably, the reaction is carried out at a reaction temperature of in the range of about −20° C. to 140° C., preferably about room temperature to the reflux temperature of the solvent.

The reaction of compounds of formula (IV) with phosphonates are carried out under conventional Horner-Emmons conditions, using any suitable, aprotic solvent for example an aromatic hydrocarbon such as benzene, toluene or xylene, DMF, DMSO, chloroform, dioxane, dichloromethane, preferably, THF, acetonitrile, N-methylpyrrolidone, and the like or mixtures thereof, preferably an anhydrous solvent, at a temperature providing a suitable rate of formation of the required product, conveniently at ambient temperature or at an elevated temperature, such as a temperature in the range of from 30° C. to 120° C.; preferably the reaction is conducted in the presence of a base. Suitable bases for use in this reaction include organic bases, such as butyl lithium, lithium diisopropylamide (LDA), N,N-diisopropylethylamine, 1,5-diazabicyclo [4.3.0]-5-nonene (DBN), 1,5-diazabicyclo[5.4.0]-5-undecene (DBU), 1,5-diazabicyclo[2.2.2]octane (DABCO), and inorganic bases, such as sodium hydride; preferably sodium hydride, and generally the reaction is carried out in an inert atmosphere such as nitrogen.

For compounds of formula (I) wherein $R_2$ and $R_4$=H, an aldehyde of formula (V) is reacted with an aliphatic aldehyde of formula (VI) (Scheme(Ib)), in presence of an inorganic base such as sodium or potassium hydroxide affording compound (II) using the appropriate conventional procedure.

Alternatively, compounds of formula (I) wherein $R_2$ and $R_4$=H may be prepared as shown in Scheme (Ic) in which a compound of formula (IV) is reacted with a substituted carbethoxymethylphosphonium salt or carbethoxymethylphosphonate, the resulting carboxylic ester (VII) is then converted into the corresponding alcohol by reduction agent, suitably using a complex metal reducing agent such as lithium aluminium hydride ($LiAlH_4$), dissobutyl aluminium hydride (DIBAH) or lithium borohydride ($LiBH_4$), in any suitable aprotic solvent for example methylene dichloride, chloroform, dioxane, diethyl ether or THF, at any temperature providing a suitable rate of formation of the required product, such as a temperature in the range of from −30° C. to 60° C., for example at room temperature. The intermediate alcohol is then oxidised to aldehyde (II) with an oxidising agent such as manganese dioxide, periodinane (Dess-Martin reagent), pyridinium chlorochromate (PCC) or pyridinium dichromate (PDC) or a combination of oxalyl chloride and DMSO (Swern reaction), preferably manganese dioxide in methylene dichloride.

The compounds of formula (III) can be prepared according to the reaction sequence shown in Scheme (II) below:

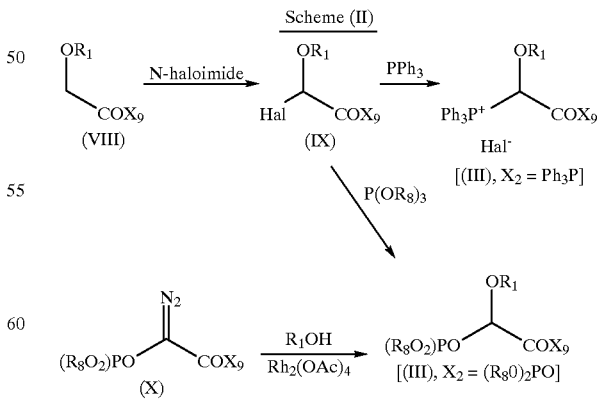

wherein, subject to any qualification mentioned below, $R_1$ and $R_8$ are as defined in relation to formula (I) and $X_9$ is as defined in relation to formula (III).

The starting material is an α-alkoxycarboxylic ester of formula (VIII) which is commercially available or which is prepared according to the methods known in the art, for example those reported in *Rodd's Chemistry of Organic Compounds*, Vol ID, p. 96 (1965), S. Coffey Ed., Elseviers. The compound of formula (VIII) is reacted with an N-haloimide, for example N-bromosuccinimide in the presence of a radical producing agent such as azobisisobutyronitrile or benzoyl peroxide in a suitable solvent such as carbon tetrachloride, benzene, for example carbon tetrachloride and at a reaction temperature in the range of from −30° C. and 80° C., for example at room temperature; examples of such a reaction may be found in the literature, for example, *J. Org. Chem.*, 41, 2846 (1976). The halocompound obtained, of formula (IX), is then reacted either with triphenylphosphine or with a trialkyl phosphite $P(OR_8)_3$ to give the required compound of formula (III) as shown in Scheme (II).

When the compound of formula (IX) is reacted with triphenylphosphine, the reaction is performed in any conventionally used solvent, for example dioxane, tetrahydrofuran, benzene, xylene or, preferably, toluene at a suitable reaction temperature in the range of from −30° C. to 80° C., for example at room temperature (examples of this conversion are reported in the literature, for example in *Chem. Ber.*, 97, 1713 (1964)).

When the compound of formula (IX) is reacted with trialkyl phosphite $P(OR_8)_3$, the reaction is performed in any conventionally used solvent, preferably the trialkyl phosphite, and at a suitable reaction temperature, preferably at the boiling point of the solvent (examples of this conversion are reported in the literature, for example in *Liebigs Ann. Chem.*, 699, 53 (1966)).

Alternatively, a compound of formula (III) in which $R_2$ is $(R_8O)_2PO$ may be prepared using the procedure depicted in Scheme (II), by reacting a diazophosphonoacetates of formula (X) with an alcohol or phenol of formula $R_1OH$, wherein $R_1$ is as defined in relation to formula (I), in the presence of rhodium$^{II}$ acetate as described in the literature, for example in *Tetrahedron*, 50, 3177 (1994) or in *Tetrahedron*, 48, 3991 (1992).

The compounds of formula (IV) wherein R4 is other than hydrogen are known compounds or they are prepared using methods analogous to those used to prepare known compounds, such as those described in *J. Org. Chem.*, 47, 757 (1982); *Heterocycles*, 22, 1211 (1984); *Tetrahedron*, 44, 443 (1988).

Also, the compounds of formula (IV) wherein $R_4$ is other than hydrogen can be prepared from aldehydes of formula (V) according to the following scheme:

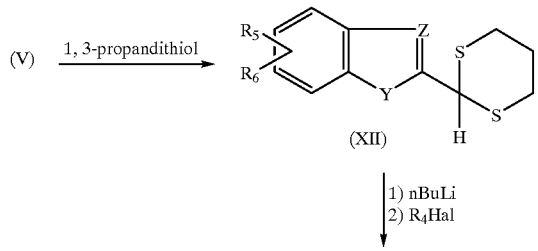

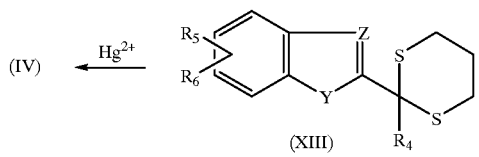

Reaction of compound (V) with 1,3-propandithiol to give compound (XII) is carried out in the presence on a catalytic amount of acid, suitably p-toluenesulphonic acid, in toluene at the refluxing temperature in a Dean-Stark apparatus and removing azeotropically the water formed. Alkylation of compound (XII) with $R_4Hal$, in which Hal is an halogen, suitably bromo or iodo, is carried out in the presence of a base such as butyl lithium in anhydrous THF under an inert athmosphere at a temperature of between −30° C. to room temperature (see, for example: *Tetrahedron*, 44, 443–450, 1988). Conversion of compound (XIII) to compound (IV) can be performed with mercury salts.

The compounds of formula (V) wherein Y is O and Z is CH, or wherein Y is N and Z is CH═CH, are commercially available compounds.

The compounds of formula (V) wherein Y is O, S or NH and Z is N or CH can be prepared by reaction of paraldehyde with a of compound formula (XI):

wherein $R_{5'}$ is $R_5$ as defined in relation to formula (I) or a protected form thereof and $R_{6'}$ is $R_6$ as defined in relation to formula (I) or a protected form thereof and X and Z are as defined in relation to formula (I).

The reaction between the compound of formula (XI) and paraldehyde is conveniently carried out in an aprotic solvent such as acetonitrile in the presence of hydrogen peroxide/ferrous sulphate, usually at an elevated temperature such as the reflux temperature of the solvent.

The compounds of formula (VI) and (VIII) are known compounds or they are prepared using methods analogous to those used to prepare known compounds, such as those described in J. March, *Advanced Organic Chemistry*, 3rd Edition (1985), Wiley Interscience.

The compounds of formula (XI) are known compounds or they are prepared using methods analogous to those used to prepare known compounds, such as those described in "*Rodd's Chemistry of Carbon compounds*", Second Edition, S. Coffey and M. F. Ansell Ed., Vol, IV, Part C, Elseviers, 1986 and Supplement to the Second Edition, M. F. Ansell Ed., Vol, IV, Part C, Elseviers, 1994

Suitable conversions of one compound of formula (I) into another compound of formula (I) includes converting a compound of formula (I) wherein X represents a hydroxy group or an alkoxy group into a compound of formula (I) wherein X represents a different alkoxy group or a moiety of the above defined formula $NR_5R_{f'}$. Such conversions are shown below in Scheme (III):

Scheme (III)

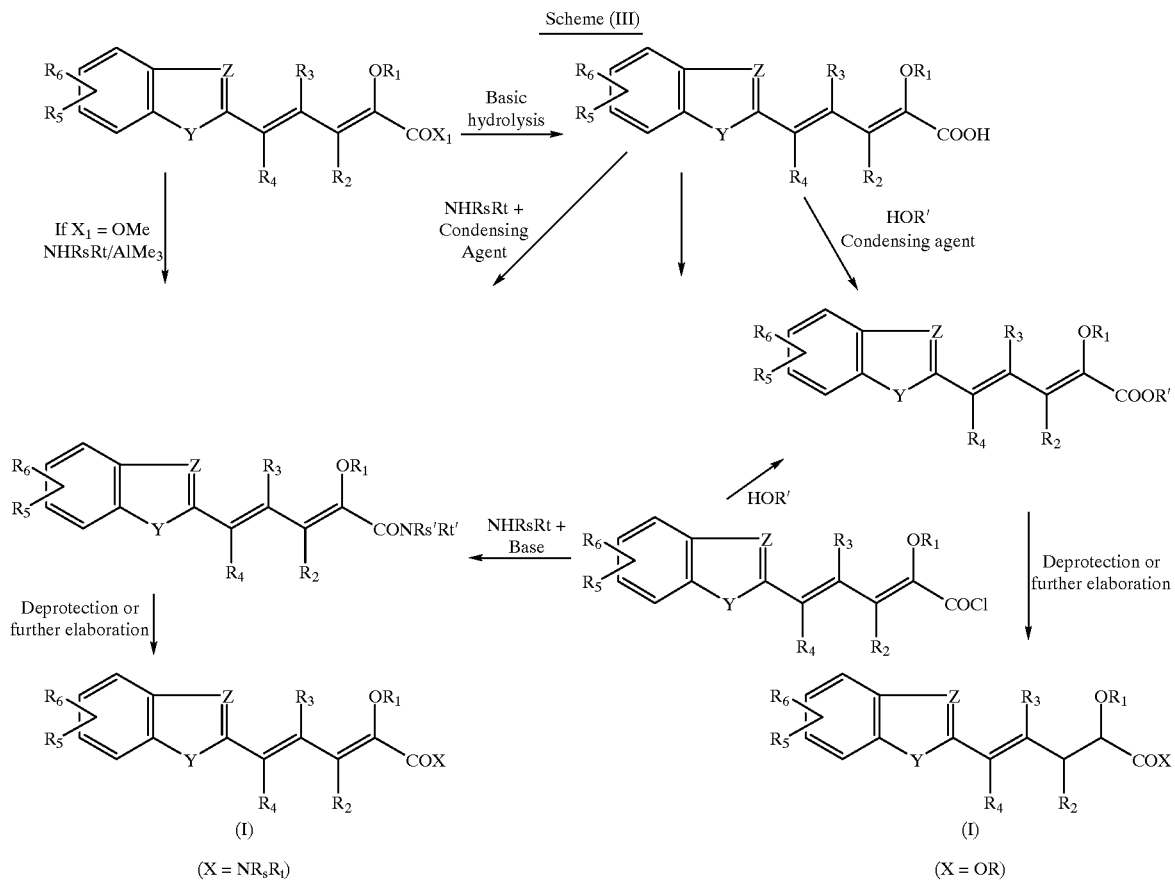

wherein, subject to any qualification mentioned below, $R_2$, $R_3$, $R_4$, $R_5$, $R_6$, $R_7$, $R_8$, X, Y and Z are as defined in relation to the compounds of formula (I), $R_{S'}$ is $R_S$ or a protected form thereof, $R_{t'}$ is $R_t$ or a protected form thereof and R' is X when X is an alkoxy group.

The conversion of one compound of formula (I) into another compound of formula (I) may be carried out using the appropriate conventional procedure; for example, the above mentioned conversion of a compound wherein X represents a hydroxy group or an alkoxy group into a compound wherein X represents a moiety of the above defined formula $NR_S R_t$ or another alkoxy group may be carried out as follows:

(i) when X is alkoxy, by basic hydrolysis, using for example potassium hydroxide, to provide a compound of formula (I) wherein X is hydroxy, and thereafter (a) for preparing compounds wherein X represents a moiety of the above defined formula $NR_S R_t$, treating with a compound of formula $HNR_{S'} R_{t'}$ wherein $R_{S'}$ and $R_{t'}$ are as defined above or (b) for preparing compounds of formula (I) wherein X represents alkoxy, by treating with a compound of formula R'OH wherein R' is the required alkoxy group; and thereafter optionally deprotecting; or (ii) when X is hydroxy, by using analogous procedures to those mentioned above in (i).

Preferably the reaction with the compounds of formula $HNR_{S'} R_{t'}$ or with compounds of formula R'OH takes place after activation of the carboxylic group.

A carboxyl group may be activated in conventional manner, for example, by conversion into an acid anhydride, acid halide, acid azide or an activated ester such as cyanomethyl ester, thiophenyl ester, p-nitrophenyl ester, p-nityrothiophenyl ester, 2,4,6-trichlorophenyl ester, pentachlorophenyl ester, pentafluorophenyl ester, N-hydroxyphthalimido ester, 8-hydroxypiperidine ester, N-hydroxysuccinimide ester, N-hydroxybenzotriazole ester, or the carboxyl group may be activated using a carbodiimide such as N,N'-dicyclohexylcarbodiimide (DCC) or 1-ethyl-3-[3-(dimethylamino)propyl]-carbodiimide hydrochloride (WSC), either in the presence or the absence of hydroxybenzotriazole (HOBt) or 1-hydroxy-7-azabenzotriazole (HOAt); or it may be activated using N,N'-carbonyldiimidazole, Woodward-K reagent, Castro's reagent or an isoxazolium salt.

Condensation of an activated carboxyl group within amino group or with an alcoholic group may be carried out in the presence of a base, in any suitable solvent.: Suitable bases include organic bases, such as triethylamine, trimethylamine, N,N-diisopropylethylamine (DIPEA), pyridine, N,N-dimethylaniline, 4-dimethylaminopyridine (DMAP), N-methylmorpholine, 1,5-diazabicyclo[4.3.0]-5-nonene (DBN), 1,5-diazabicyclo[5.4.0]-5-undecene (DBU), 1,5-diazabicyclo[2.2.2]octane (DABCO), and inorganic bases, such as potassium carbonate. Suitable solvents include conventionally used solvents, for example DMF, dimethyl sulfoxide (DMSO), pyridine, chloroform, dioxane, dichloromethane, THF, ethyl acetate, acetonitrile, N-methylpyrrolidone and hexamithlphosphoric triamide and mixtures thereof. The reaction temperature may be within the usual temperature range employed in this type of condensation reaction, and generally in the range of about −40° C. to about 60° C., preferably from about −20° C. to about 40° C.

When the reaction is carried out in the presence of a suitable condensing agent, for example a carbodiimide, N,N'- carbonyldiimidazole, Woodward-K reagent, Castro's reagent or the like, the condensing agent is preferably employed in an amount from equimolar to about 5 times the molar quantity of the starting material and the reaction is performed in a suitable solvent for example a halogenated hydrocarbon such as dichloromethane, chloroform, carbon tetrachloride, tetrachloroethane or the like; an ether such as dioxane, THF, dimethoxyethane or the like, a ketone such as acetone, methyl ethyl ketone or the like; acetonitrile, ethyl acetate, DMF, dimethylacetamide, DMSO or the like. Preferably the condensation is carried out in an anhydrous solvent, and at a reaction temperature in the range of from about −10° C. to 60° C., preferably about 0° C. to room temperature.

Alternatively, conversion of one compound of formula (I) in which X is O-alkyl into another compound of formula (I) in which X is $NR_S R_t$ may be effected by treating the said compound of formula (I) directly with a compound of formula $HNR_S R_t$, in the presence of a trialkylaluminium reagent such as trimethylaluminium or triethylaluminium, according to known procedures, such as those disclosed in *Tetrahedron Lett.*, 48, 4171 (1977); and, if necessary, deprotecting or converting the compound of formula (I) in which X is $NR_{S'} R_{t'}$ into a compound of formula (I) in which X is $NR_S R_t$.

The trialkylaluminium reagent is generally employed in the above mentioned reactions in an amount of from equimolar to about 5 times the molar quantity of the starting material, preferably 2–3 times the molar quantity of the starting material and the reaction is performed in a suitable solvent for example a halogenated hydrocarbon such as dichloromethane, chloroform, carbon tetrachloride, tetrachloroethane or the like; and ether such as dioxane, THF, dimethoxyethane or the like. Preferably the condensation is carried out in an anhydrous solvent, and at a reaction temperature of about, generally −20° C. to 120° C., preferably about 0° C. to the reflux temperature of the solvent.

Amines of general formula $HNR_S R_t$ may be prepared using the methods known in the art for the preparation of amines, for example as taught in *Houben-Weil, Methoden der Organischen Chemie*, Vol. XI/1 (1975) and Vol. E16d/2 (1992), Georg Thieme Verlag, Stuttgart.

In particular, amines of the general formula $HNR_S R_t$ wherein one of $R_S$ and $R_t$ represents hydrogen and the other represents a moiety (a), (b), (c), (d) (e) as defined above or a particular example thereof, are prepared according to the methods summarised in Scheme (IV) below:

Scheme (IV)

Scheme (IV)

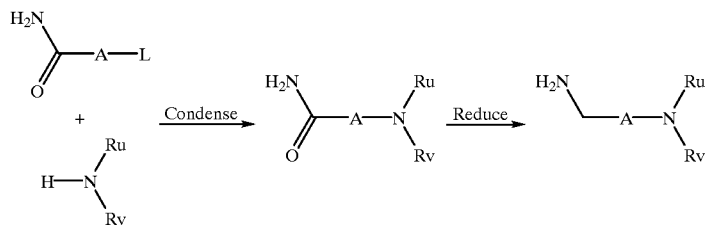

(i)

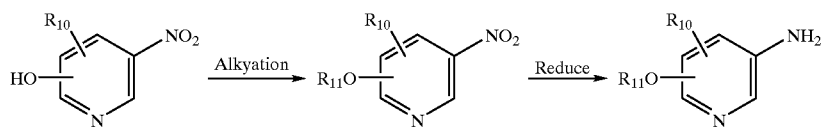

(ii)

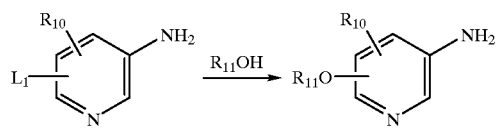

(iii)

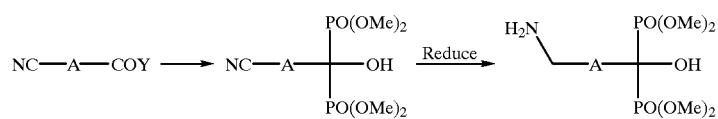

(iv)

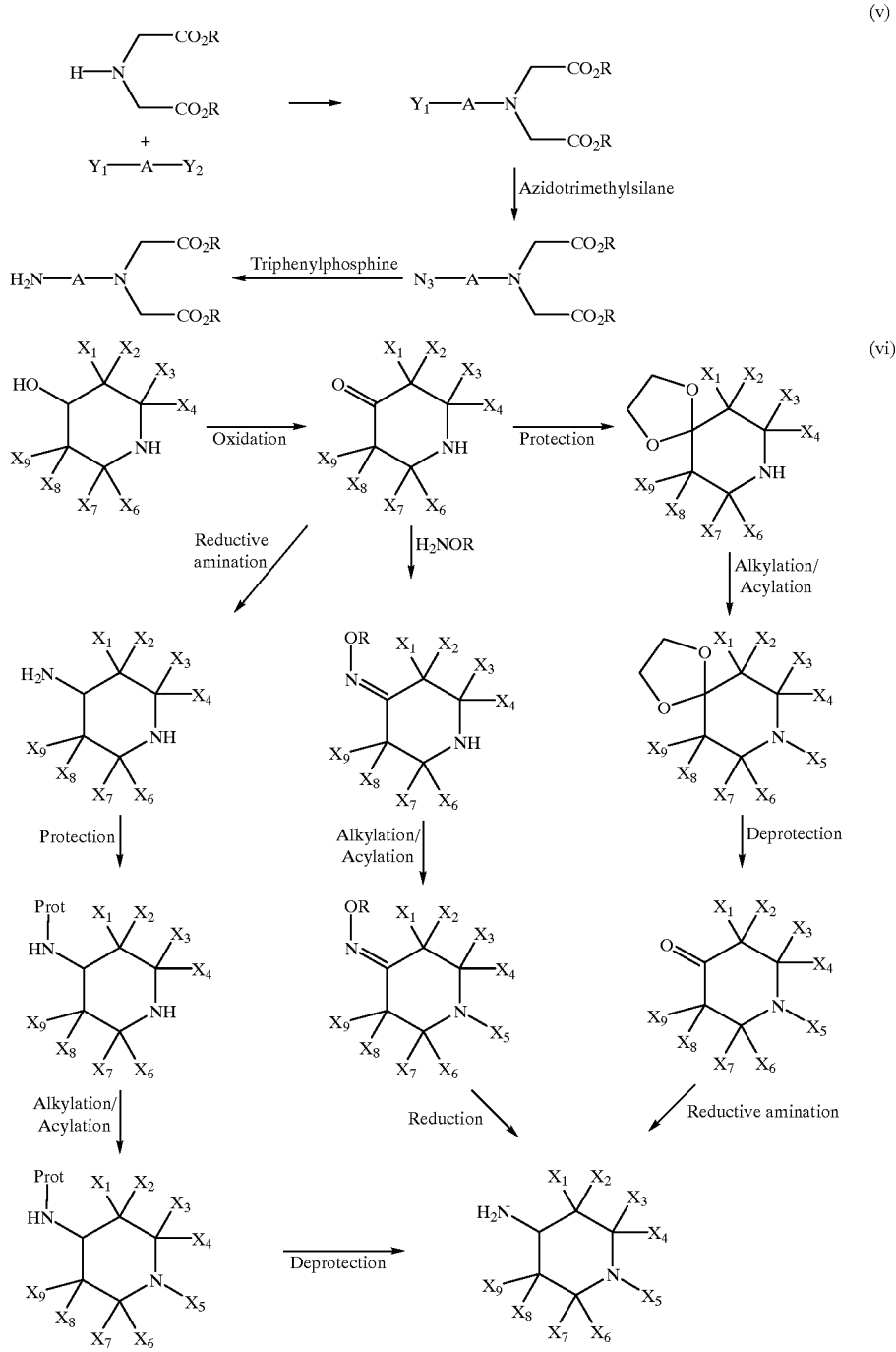

wherein R is an alkyl or aryl group, $R_u$ and $R_v$ are as defined above, $X_1$ to $X_9$ are as defined for (H2), A is a bond or an alkyl chain, $R_{10}$ is hydrogen (in ii) or halogen (in(iii)) and $R_{11}$ is an alkyl group, $R_{12}$ is alkyl or aryl, L and $L_1$ are leaving groups, for example halogen or mesylate, Y is halogen, $Y_1$ is a leaving group, for example a halogen and and $Y_1$ and $Y_2$ are leaving groups such as halogens, for example $Y_1$ is chloride and $Y_2$ is bromine.

With regard to Scheme (IV):

The reduction of the amide functioning (i) is suitably carried out using known methods, for example by using mixed hydride reducing agents, such as lithium aluminium hydride and methods described in Org Synth Coll Vol 4 564.

The reduction of the nitropyridine in (ii) is suitably carried out using the method described in J. Org. Chem. 58, 4742 (1993).

The alkylation of the hydroxy-nitropyridine in (ii) may be effected by using the method described in J. Org. Chem 55, 2964 (1990).

The displacement reaction in (iii) is suitably carried out using the method described in Helvetica Chemica Acta 47 (2), 45 (1964)

The reduction of the nitrile in (v) is suitably carried by catalytic hydrogenation over platinium oxide.

The reaction of acid halid NC-A-COY to provide the dialkylphosphonate in (iv) is effected by following the procedure described in *J Org Chem* 36, 3843 (1971).

The reaction of the azide with triphenylphosphine in (v) is carried out in wet tetrahydrofuran as described in *Bull Soc Chim Fr* 1985, 815.

The azides in (v) are prepared as shown using azidotrimethylsilane, following the procedure described in *Synthesis* 1995, 376.

The reaction of compound $Y_1$-A-$Y_2$ and the amine derivative in (v) proceeds under conventional displacement reaction conditions.

The reactions in (vi) can be performed using known, conventional methods, as described in J. March, *Advanced Organic Chemistry*, 3rd Edition, 1985, Wiley Interscience. For example, oxidation can be performed using oxidising agents such as chromic acid (Jones reagent); reductive amination of the ketone in can be performed with benzylamine to give an imine intermediate which is then reduced using known methods and reducing agents such as sodium borohydride or lithium aluminium hydride. Debenzylation can then be performed again using conventional methods, for example with hydrogen in the presence of a catalyst such as palladium on charcoal. Protection of ketone as the ethylene ketal can be performed with ethylene glycol under acidic catalysis; acylaions or alkylations can be performed by treating the suitable piperidine derivatives with acyl or alkyl halides in the presence of an inorganic or organic base; deprotection of the dioxolane to the ketone can be effected by acidic treatment in aqueous or alcoholic solvents. Protection on the primary amino group in 4 aminopiperidines can entail the use of classical carbamate protecting agents such as t-butoxycarbonyl (BOC), benzyloxycarbonyl (CBZ) or fluorenylmethoxycarbonyl (FMOC), or of the phthalimido protecting group: the synthesis and the removal of such protective groups is described in, for example, in *Protective Groups in Organic Synthesis*, T. W. Greene Ed., Wiley, New York, 1981. 4-Oxopiperidines can be converted into the corresponding oximes by treatment with hydroxyl- or alkoxyl-amine in a suitable solvent: reduction of the oxime to amine can be performed using conventional reducing agents such as lithium aluminium hydride or sodium cyanoborohydryde.

The starting materials in the above reactions (i), (ii), (iii), (iv), (v) and (vi) are known commercially available compounds.

A compound of formula (I) or a solvate thereof may be isolated from the above mentioned processes according to standard chemical procedures.

The preparation of salts and/or solvates of the compounds of formula (I) may be performed using the appropriate conventional procedure.

If required mixtures of isomers of the compounds of the invention may be separated into individual stereoisomers and disatereoisomers by conventional means, for example by the use of an optically active acid as a resolving agent. Suitable optically active acids which may be used as resolving agents are described in "*Topics in Stereochemistry*", Vol. 6, Wiley Interscience, 1971, Allinger, N. L. and Eliel, W. L. Eds.

Alernatively, any enantiomer of a compound of the invention may be obtained by stereospecific synthesis using optically pure starting materials of known configuration.

The absolute configuration of compounds may be determined by conventional methods such as X-ray crystallographic techniques.

The protection of any reactive group or atom, may be carried out at an appropriate stage in the aforementioned processes. Suitable protecting groups include those used conventionally in the art for the particular group or atom being protected. Protecting groups may be prepared and removed using the appropriate conventional procedure, for example OH groups, including diols, may be protected as the silylated derivatives by treatment with an appropriate silylating agent such as di-tert-butylsilylbis (trifluoromethanesulfonate): the silyl group may then be removed using conventional procedures such as treatment with hydrogen fluoride, preferably in the form of a pyridine complex and optionally in the presence of alumina, or by treatment with acetyl chloride in methanol. Alternatively benzyloxy groups may be used to protect phenolic groups, the benzyloxy group may be removed using catalytic hydrogenolysis using such catalysts as palladium (II) chloride or 10% palladium on carbon.

Amino groups may be protected using any conventional protecting group, for example tert-butyl esters of carbamic acid may be formed by treating the amino group with di-tert-butyldicarbonate, the amino group being regenerated by hydrolysing the ester under acidic conditions, using for example hydrogen chloride in ethyl acetate or trifluoroacetic acid in methylene dichloride. An amino group may be protected as a benzyl derivative, prepared from the appropriate amine and a benzyl halide under basic conditions, the benzyl group being removed by catalytic hydrogeneolysis, using for example a pallaium or carbon catalyst.

Indole NH groups and the like may be protected using any conventional group, for example benzenesulphonyl, methylsulphonyl, tosyl, formyl, acetyl (all of them removable by treatment with alkaline reagents), benzyl (removable either with sodium in liquid ammonia or with $AlCl_3$ in toluene), allyl (removable by treatment with rhodium (III) chloride under acidic conditions), benzyloxycarbonyl (removable either by catalytic hydrogenation or by alkaline treatment), trifluoroacetyl (removable by either alkaline or acidic treatment), t-butyldimethylsilyl (removable by treatment with tetrabutylammonium fluoride), 2-(trimethylsilyl) ethoxymethyl (SEM) (removable by treatment with tetrabutylammonium fluoride in the presence of ethylendiamine), methoxymethyl (MOM) or methoxyethyl (MEM) groups (removed by mild acidic treatment).

Carboxyl groups may be protected as alkyl esters, for example methyl esters, which esters may be prepared and removed using conventional procedures, one convenient method for converting carbomethoxy to carboxyl is to use aqueous lithium hydroxide.

A leaving group or atom is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

The salts, esters, amides and solvates of the compounds mentioned herein may as required be produced by methods conventional in the art: for example, acid addition salts may be prepared by treating a compound of formula (I) with the appropriate acid.

Esters of carboxylic acids may be prepared by conventional esterification procedures, for example alkyl esters may be prepared by treating the required carboxylic acid with the appropriate alkanol, generally under acidic conditions.

Amides may be prepared using conventional amidation procedures, for example amides of formula $CONR_5R_t$ may be prepared by treating the relevant carboxylic acid with an amine of formula $HN\ R_SR_t$ wherein $R_S$ and $R_t$ are as defined above. Alternatively, a $C_{1-6}$ alkyl ester such as a methyl ester of the acid may be treated with an amine of the above defined formula $HNR_SR_t$ to provide the required amide.

As mentioned above the compounds of the invention are indicated as having useful therapeutics properties:

The present invention therefore provides a method for the treatment and/or prophylaxis of diseases associated with over activity of ostoclasts in mammals which method comprises the administration of an effective non-toxic amount of a selective inhibitor of mammalian osteoclasts.

A suitable selective inhibitor of a mammalian osteoclast is a selective inhibitor of the vacuolar ATPase located on the ruffled border of mammalian osteoclasts.

One particular selective inhibitor of mammalian vacuolar ATPase is a compound of formula (I), or a pharmaceutically acceptable salt thereof, or a pharmaceutically acceptable solvate thereof.

Thus, the present invention further provides a method for the treatment of osteoporosis and related osteopenic diseases in a human or non-human mammal, which comprises administering an effective, non-toxic, amount of a compound of formula (I) or a pharmaceutically acceptable solvate thereof, to a human or non-human mammal in need thereof.

In a further aspect, the present invention provides an inhibitor of a mammalian osteoclasts, for example a compound of formula (I) or a pharmaceutically acceptable salt thereof, or a pharmaceutically acceptable solvate thereof, for use as an active therapeutic substance.

In particular the present invention provides a compound of formula (I) or a pharmaceutically acceptable salt thereof and/or a pharmaceutically acceptable solvate thereof, for use in the treatment of and/or phophylaxis of osteoporosis and related osteopenic diseases.

Of particular interest is the osteoporosis associated with the peri and post menopausal conditions. Also encompassed are the treatment and prophylaxis of Paget's disease, hypercalcemia associated with bone neoplasms and all the types of osteoporotic diseases as classified below according to their etiology:

Primary osteoporosis
Involutional
Type I or postmenopausal
Type II or senile
Juvenile
Idiopathic in young adults
Secondary osteoporosis
Endocrine abnormality
Hyperthyroidism
Hypogonadism
Ovarian agenesis or Turner's syndrome
Hyperadrenocorticism or Cushing's syndrome
Hyperparathyroidism
Bone marrow abnormalities
Multiple myeloma and related disorders
Systemic mastocytosis
Disseminated carcinoma
Gaucher's disease
Connective tissue abnormalities
Osteogenesis imperfecta
Homocystinuria
Ehlers-Danlos syndrome
Marfan's syndrome
Menke's syndrome
Miscellaneous causes
Immobilisation or weightlessness
Sudeck's atrophy
Chronic obstructive pulmonary disease
Chronic alcoholism
Chronic heparin administration
Chronic ingestion of anticonvulsant drugs In addition the invention encompasses the treatment of tumours, especially those related to renal cancer, melanoma, colon cancer, lung cancer and leukemia, viral conditions (for example those involving Semliki Forest virus, Vesicular Stomatitis virus, Newcastle Disease virus, Influenza A and B viruses, HIV virus), ulcers (for example chronic gastritis and peptic ulcer induced by *Helicobacter pylori*), for use as immunosupressant agents in autoimmune diseases and transplantation, antilipidemic agents for the treatment and/or prevention of hypercholesterolemic and atherosclerotic diseases and to be useful for the treatment of AIDS and Alzheimers's disease. These compounds are also considered useful in treating angiogenic diseases, i.e. those pathological conditions which are dependent on angiogenesis, such as rheumatoid arthritis, diabetic retinopathy, psoriasis and solid tumours.

A compound of formula (I), or a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention also provides a pharmaceutical composition comprising a selective inhibitor of the pharmacological activity of human osteoclast cells, in particular the bone resorption activity of human osteoclast cells associated with abnormal loss of bone mass, and a pharmaceutically acceptable carrier thereof.

A particular inhibitor of human osteoclast cells is a selective inhibitor of human osteoclast vacuolar ATPase such as a compound of formula (I), or a pharmaceutically acceptable salt thereof, or a pharmaceutically acceptable solvate thereof, and a pharmaceutically acceptable carrier thereof.

Active compounds or a pharmaceutically acceptable salt thereof and/or a pharmaceutically acceptable solvate thereof is normally administered in unit dosage form.

An amount effective to treat the disorders hereinbefore described depends upon such factors as the efficacy of the active compounds, the particular nature of the pharmaceutically acceptable salt or pharmaceutically acceptable solvate chosen, the nature and severity of the disorders being treated and the weight of the mammal. However, a unit dose will normally contain 0.01 to 50 mg, for example 1 to 25 mg, of the compound of the invention. Unit doses will normally be administered once or more than once a day, for example 1, 2, 3, 4, 5 or 6 times a day, more usually 1 to 3 or 2 to 4 times a day such that the total daily doses is normally in the range, for a 70 kg adult of 0.01 to 250 mg, more usually 1 to 100 mg, for example 5 to 70 mg, that is in the range of approximately 0.0001 to 3.5 mg/kg/day, more usually 0.01 to 1.5 mg/kg/day, for example 0.05 to 0.7 mg/kg/day.

At the above described dosage range, no toxicological effects are indicated for the compounds of the invention.

The present invention also provides a method for the treatment of tumours, especially those related to renal cancer, melanoma, colon cancer, lung cancer and leukemia, viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases. AIDS and Alzheimer's disease, angiogenic diseases, such as rheumatoid arthritis, diabetic retinopathy, psoriasis and solid tumours, in a human or non-human mammal, which comprises administering an effective, non-toxic, amount of a compound of formula (I) or a pharmaceutically acceptable solvate thereof, to a human or non-human mammal in need thereof.

In such treatments the active compound may be administered by any suitable route, e.g. by the oral, parenteral or topical routes. For such use, the compound will normally be employed in the form of a pharmaceutical composition in association with a human or veterinary pharmaceutical carrier, diluent and/or excipient, although the exact form of the composition will naturally depend on the mode of administration.

Compositions are prepared by admixture and are suitably adapted for oral, parenteral or topical administration, and as such may be in the form of tablets, capsules, oral liquid preparations, powders, granules, lozenges, pastilles, reconstitutable powders, injectable and infusable solutions or suspensions, suppositories and transdermal devices. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solution, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filer sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the active compound.

For topical administration, the composition may be in the form of a transdermal ointment or patch for systemic delivery of the active compound and may be prepared in a conventional manner, for example, as described in the standard textbooks such as *'Dermatological Formulations'*- B. W. Barry (Drugs and the Pharmaceutical Sciences - Dekker) or Harrys Cosmeticology (Leonard Hill Books).

The present invention also provides the use of a selective inhibitor of the biological activity of human osteoclast cells, in particular the bone resorption activity of human osteoclast cells associated with abnormal loss of bone mass, compound of formula (I), or a pharmaceutically acceptable salt thereof, or a pharmaceutically acceptable solvate thereof, for the manufacture of a medicament for the treatment and/or prophylaxis of diseases associated with over activity of osteoclasts in mammals, such as the treatment and/or prophylaxis of osteoporosis and related osteopenic diseases.

The present invention also provides the use of a selective inhibitor of the biological activity of human osteoclast cells, in particular the bone resorption activity of human osteoclast cells associated with abnormal loss of bone mass, for the manufacture of a medicament for the treatment of tumours, especially those related to renal cancer, melanoma, colon cancer, lung cancer and leukemia., viral conditions (for example those involving Semliki Forest, Vesicular Stomatitis, Newcastle Disease, Influenza A and B, HIV viruses), ulcers (for example chronic gastritis and peptic ulcer induced by *Helicobacter pylori*), autoimmune diseases and transplantation, for the treatment and/or prevention of hypercholesterolemic and atherosclerotic diseases, AIDS and Alzheimer's disease, angiogenic diseases, such as rheumatoid arthritis, diabetic retinopathy, psoriasis and solid tumours,.

No unacceptable toxicological effects are expected with compounds of the invention when administered in accordance with the invention. As is common practice, the compositions will usually be accompanied by written or printed directions for use in the medical treatment concerned.

The following, descriptions, examples and pharmacological methods illustrate the invention but do not limit it in any way.

Preparation 1

(E)-3-(Benzofuran-2-yl)-prop-2-enal. A solution of benzofuran-2-carboxaldehyde (2.2 g, 15.1 mmol) and formylmethylenetriphenylphosphorane (4.6 g, 15.1 mmoles) in $CH_2Cl_2$ (150 mL) was refluxed for 6 hours. Another aliquot of formylmethylenetriphenylphosphorane (1.5 g, 4.93 mmol) was then added and the reflux continued overnight. The reaction mixture was cooled to RT, the solvent concentrated at reduced pressure and the residue was chromatographed on silicagel (n-heptane/EtOAc 4/1). The collected fractions were pooled and concentrated and the residue triturated with isopropyl ether to give, after drying, pure title compound (1.3 g, 7.55 mmol, yield 50.0%) as pale yellow crystals, m.p.=67°.

EXAMPLE 1

Methyl (2Z,4E)-5-(benzofuran-2-yl)-2-methoxy-2,4-pentadienoate. A suspension of methyl 2-methoxy-2-triphenylphosphonium acetate (4.45 g, 10.0 mmol) and DBU (1.52 g, 10.0 mmol) in $CH_2Cl_2$ (25 ml) was stirred at RT for 15 minutes. Then (E)-3-(benzofuran-2-yl)-propenal (1.12 g, 6.50 mmol) was added and stirring continued for 3 hours. The reaction mixture was washed with 1N HCl (10 ml), with 5% aqueous $NaHCO_3$ (10 ml) and brine (2×10 ml). The organic solution was dried ($MgSO_4$) and concentrated to give an oil that was chromatographed on silicagel (n-heptane/EtOAc 4/1). The pooled fractions were collected and concentrated to give pure title compound (1.05 g, 4.07 mmol, yield 62.5%) as pale yellow crystals, m.p.=108°.

$^1$H-NMR ($CDCl_3$): 7.54 (d, 1H); 7.48 (d, 1H); 7.16-7.40 (m, 3H); 6.87 (d, 1H); 6.73 (s, 1H); 6.69 (d, 1H); 3.84 (s, 6H).

EXAMPLE 2

(2Z,4E)-5-(Benzofuran-2-yl)-2-methoxy-2,4-pentadienoic acid. To a stirred solution of methyl (2Z,4E)-5-(benzofuran-2-yl)-2-methoxy-2,4-pentadienoate (1.0 g, 3.87 mmol) in EtOH/water 1/1 (80 ml) potassium hydroxide (0.43 g, 7.66 mmol) was added. The solution was refluxed for 1 hour, then it was cooled to RT and poured into water (200 ml). After acidification to pH 2 (1N HCl) the resulting suspension was extracted with EtOAc (3×50 ml). The organic phase was washed with water (2×30 ml), dried ($MgSO_4$) and concentrated to give a yellow solid. This was repeatedly washed with $CH_2Cl_2$ and dried to give the pure title compound (0.80 g, 3.28 mmoles, yield 84.6%) as yellow crystals, m.p.=206°.

$^1$H-NMR (DMSO-$d_6$): 12.90 (bs, 1H); 7.60 (bs, 2H); 7.10-7.32 (m, 4H); 7.02 (s, 1H); 6.88 (t, 1H); 3.73 (s, 3H).

EXAMPLE 3

(2Z,4E)-5-(Benzofuran-2-yl)-2-methoxy-N-((2,2,6,6-tetramethyl)-piperidin-4-yl)-2,4-pentadienamide. A solution of (2Z,4E)-5-(benzofuran-2-yl)-2-methoxy-2,4-pentadienoic acid (122 mg, 0.5 mmol), 4-amino-2,2,6,6-tetramethylpiperidine (78 mg, 0.5 mmol), 1-hydroxy-7-azabenzotriazole hydrate (65 mg, 0.5 mmol) and 1-(3-dimethylaminopropyl)-3-ethylcarbodiimide hydrochloride (95 mg, 0.5 mmol) in DMF (2 ml) was stirred at RT for 6 hours. The solution was poured into brine (20 ml) and repeatedly extracted with EtOAc. The organic phase was washed with 5% aqueous $CaCO_3$, dried ($MgSO_4$) and concentrated to give a solid that was repeatedly washed with isopropyl ether. After drying pure title compound (45 mg, 0.12 mmol, yield 23.5%) was obtained as pale yellow crystals, mp.=250° dec.

$^1$H-NMR (DMSO-$d_6$): 9.33 (bs, 1H); 8.35 (d, 1H); 7.60 (t, 2H); 7.24-7.36 (m, 2H); 7.15 (dd, 1H); 7.00 (s, 1H); 6.90 (d, 1H); 6.63 (d, 1H); 4.21 (m, 1H); 3.71 (s, 3H); 1.83 (bd, 2H); 1.67 (bt, 2H); 1.43 (s, 12H).

EXAMPLE 4

(2Z,4E)-5-(Benzofuran-2-yl)-2-methoxy-N-(3-diethylaminopropyl)-2,4-pentadienamide. A solution of (2Z,4E)-5-(benzofuran-2-yl)-2-methoxy-2,4-pentadienoic acid (122 mg, 0.5 mmol), 3-diethylaminopropylamine (65 mg, 0.5 mmol), 1-hydroxy-7-azabenzotriazole hydrate (65 mg, 0.5 mmol) and 1-(3-dimethylaminopropyl)-3-ethylcarbodiimide hydrochloride (95 mg, 0.5 mmol) in DMF (2 ml) was stirred at RT overnight. After the same work-up described in example 3 the residue was chromatographed on silicagel (preparative TLC, EtOAc/MeOH/aq.$NH_3$ 8/2/1). The fraction collected was dried to give pure title compound (32 mg, O90 mmol, yield 18.0%) as pale brown crystals, m.p.=79°.

$^1$H-NMR (DMSO-$d_6$): 8.37 (bt, 1H); 7.61 (t, 2H); 7.21-7.34 (m, 2H); 7.15 (dd, 1H); 7.00 (s, 1H); 6.90 (d, 1H); 6.66 (d, 1H); 3.72 (s, 3H); 3.20 (q, 2H); 2.46 (bm, 6H); 1.60 (bt, 2H); 0.96 (t, 6H).

Preparation 2

1,2,2,6,6-Pentamethyl-4-piperidone hydroiodide. A solution of 2,2,6,6-tetramethyl-4-piperidone monohydrate (40 g, 23.1 mmol) and methyl iodide (98.31 g, 69.3 mmol) in isopropyl alcohol (25 mL) was stirred at RT for 48 h. The resulting suspension was filtered, the solid residue was dried and recrystallized from MeOH. After filtration and repeated washings with MeOH the solid was dried giving pure title compound (31.6 g, 10.6 mmol, yield 46.0%) as pale brown crystals.

Preparation 3

1,2,2,6,6-Pentamethyl-4-piperidone oxide. A suspension of 1,2,2,6,6-pentamethyl-4-piperidone hydroiodide (3 g, 10.0 mmol) and hydroxylamine hydrochloride (980 mg, 14 mmol) in water (6 ml) was stirred at RT for 15 min. Solid NaOH was added until basic pH and thickening of the suspension. Water (3 ml) was added and stirring at RT was continued overnight. The suspension was filtered and the solid washed with water (few ml) and dried. The solid was then dissolved in $Et_2O$, the solution was dried ($MgSO_4$) and concentrated to give after drying pure title compound (1.55 g, 8.41 mmol, yield 83.3%) as white crystals.

Preparation 4

4-Amino-1,2,2,6,6-pentamethyl-4-piperidine. $LiAlH_4$ (925 mg, 24.4 mmol) was added under stirring at 0° under Ar to anhydrous THF (100 ml), followed by 1,2,2,6,6-pentamethyl-4-piperidone oxime (1.50 g, 8.14 mmol). The suspension was refluxed for 2 hours, then cooled to RT and stirred overnight. After cooling to 0° water (0.9 ml), 15% aqueous NaOH (0.9 ml) and water (2.8 ml) were carefully added dropwise. The suspension was stirred for 15 min at RT, then $MgSO_4$ was added and stirring continued for 30 min. After filtration, the liquid was concentrated and the oily residue chromatographed on silicagel ($CH_2Cl_2$/MeOH/aq.$NH_3$ 95/5/1). The collected fractions were pooled and concentrated to give pure title compound (750 mg, 4.40 mmol, yield 54.1%) as a yellow oil.

EXAMPLE 5

(2Z,4E)-5-(Benzofuran-2-yl)-2-methoxy-N[(1,2,2,6,6-pentamethyl)-piperidin-4-yl]-2,4-pentadienamide. A solution of (2Z,4E)-5-(benzofuran-2-yl)-2-methoxy-2,4-pentadienoic acid (122 mg, 0.5 mmol), 4-amino-1,2,2,6,6-pentamethylpiperidine (85 mg, 0.5 mmol), 1-hydroxy-7-azabenzotriazole hydrate (65 mg, 0.5 mmol) and 1-(3-dimethylaminopropyl)-3-ethylcarbodiimide hydrochloride (95 mg, 0.5 mmol) in DMF (2 ml) was stirred at RT overnight. After the same work-up described in example 3 the residue was triturated with isopropyl ether to produce a solid that was recovered and dried to give pure title compound (85 mg, 0.214 mmol, yield 42.8%) as yellow crystals, m.p.=152°.

$^1$H-NMR (DMSO-$d_6$): 8.07 (bd, 1H); 7.61 (t, 2H); 7.22-7.36 (m, 2H); 7.14 (dd, 1H); 7.00 (s, 1H); 6.89 (d, 1H); 6.60 (d, 1H); 4.10 (m, 1H); 3.71 (s, 3H); 2.27 (s, 3H); 1.50-1.72 (bm, 4H); 1.12 (d, 12H).

Preparation 5

5-Chlorobenzofuran-2-carboxylic acid. A suspension of 5-chlorosalicyl aldehyde (10.62 g, 67.8 mmol), ethyl bromomalonate (25.3 g, 105.8 mmol) and anhydrous potassium carbonate (9.37 g, 67.8 mmol) in ethylmethylketone (50 ml) was refluxed for 5 hours, then kept under stirring at RT overnight. The solvent was evaporated and the residue was diluted with water (500 ml), then the pH was neutralized with 1N HCl. The suspension was extracted with $Et_2O$, then the organic phase was dried ($MgSO_4$) and concentrated. The oily residue was dissolved in absolute EtOH (50 ml) and added to a 10% ethanolic solution of KOH. The thick suspension was refluxed under vigorous stirring overnight then after cooling to RT the solvent was taken off and water was added. The aqueous phase was washed with $Et_2O$, then the pH adjusted to 2 with 1N HCl. The aqueous suspension was extracted with EtOAc and the organic phase after drying ($MgSO_4$) and concentration produced pure title compound (7.4 g, 37.6 mmol, yield 55.5%) as a yellow oil.

Preparation 6

5-Chlorobenzofuran-2-carboxaldehyde. $LiAlH_4$ (3.04 g, 80 mmol) was suspended under stirring at 0° under Ar in anhydrous THF (150 ml), then N-methylpiperazine dihydrochloride (6.92 g, 40 mmol) was added portionwise in 10 minutes. N-methylpiperazine (12 g, 120 mmol) was then added dropwise, the mixture was warmed to RT and stirring continued for 2 hours. The surnatant of this suspension was then added by syringe to a stirred solution at 0° under Ar of 5-chlorobenzofuran-2-carboxylic acid (2.95 g, 15.0 mmol) in anhydrous THF (50 ml). The mixture was refluxed for 4 hours and after cooling to RT the suspension was diluted with $Et_2O$ (400 ml). The resulting mixture was poured into water (500 ml) and the organic phase was decanted. The aqueous phase was extracted with $Et_2O$ (2×300 ml) and the pooled organic extracts were washed with 2N NaOH (200 ml), 1N HCl (200 ml) and brine (200 ml). After drying ($MgSO_4$) and concentration a brown oily residue was obtained. This was chromatographed on silicagel (n-heptane/EtOAc 3/1). The pooled fractions produced after evaporation pure title compound (850 mg, 4.71 mmol, yield 31.4%) as brown needles.

Preparation 7

(E)-3-(5-Chlorobenzofuran-2-yl)-prop-2-enal. A solution of 5-chlorobenzofuran-2-carboxaldehyde (813 mg, 4.50 mmol) and formylmethylene triphenylphosphorane (1.37 g, 4.50 mmol) in $CH_2Cl_2$ (40 ml) was treated as sen in preparation 1. After a chromatography on silicagel (n-heptane/EtOAc 4/1) pure title compound (640 mg, 3.10 mmol, yield 68.8%) as yellow crystals was obtained.

EXAMPLE 6

Methyl (2Z,4E)-5-(5-chlorobenzofuran-2-yl)-2-methoxy-2,4-pentadienoate. A suspension of methyl 2-methoxy-2-triphenylphosphonium acetate (1.80 g, 4.04 mmol) and DBU (610 mg, 4.04 mmol) in $CH_2Cl_2$ (20 ml) was stirred at RT for 15 minutes. Then (2E)-3-(5-chlorobenzofuran-2-yl)-propenal (465 mg, 2.25 mmol) was added and the reaction conducted as seen for example 1. After a chromatography on silicagel (n-heptane/EtOAc 4/1) pure title compound (550 mg, 1.78 mmol, yield 79.2%) as yellow crystals was obtained.

$^1$H-NMR (DMSO-$d_6$): 7.70 (d, 1H); 7.65 (d, 1H); 7.36 (dd, 1H); 7.20 (dd, 1H); 7.05 (s, 1H); 6.97 (d, 1H); 6.91 (d, 1H); 3.77 (s, 3H); 3.74 (s, 3H).

EXAMPLE 7

(2Z,4E)-5-(5-Chlorobenzofuran-2-yl)-2-methoxy-2,4-pentadienoic acid. To a stirred solution of methyl (2Z,4E)-5-(5-chlorobenzofuran-2-yl)-2-methoxy-2,4-pentadienoate (530 mg, 1.81 mmol) in EtOH/water 1/1 (40 ml) potassium hydroxide (0.43 g, 7.66 mmol) was added. The solution was stirred at RT overnight, then it was treated as seen in example 2. Pure title compound (330 mg, 1.18 mmol, yield 65.4%) was obtained as bright yellow crystals.

$^1$H-NMR (DMSO-$d_6$): 7.68 (d, 1H); 7.63 (d, 1H); 7.33 (d, 1H); 7.20 (dd, 1H); 6.97 (s, 1H); 6.90 (d, 1H); 6.73 (d, 1H); 3.75 (s, 3H).

EXAMPLE 8

(2Z,4E)-5-(5-Chlorobenzofuran-2-yl)-2-methoxy-N-(1,2,2,6,6-pentamethyl)-piperidin-4-yl)-2,4-pentadienamide. A solution of (2Z,4E)-5-(5-chlorobenzofuran-2-yl)-2-methoxy-2,4-pentadienoic acid (88 mg, 0.32 mmol), 4-amino-1,2,2,6,6-pentamethylpiperidine (60 mg, 0.35 mmol), 1-hydroxy-7-azabenzotriazole hydrate (44 mg, 0.32 mmol) and 1-(3-dimethylamino propyl)-3-ethylcarbodiimide hydrochloride (62 mg, 0.5 mmol) in DMF (2 ml) was stirred at RT for 6 hours. After the same work up as seen in example 3 pure title compound was obtained (55 mg, 0.128 mmol, yield 40.0%) as bright yellow crystals, m.p.=142°.

$^1$H (DMSO-$d_6$): 8.01 (d, 1H); 7.69 (d, 1H); 7.63 (d, 1H); 7.33 (dd, 1H); 7.18 (dd, 1H); 6.98 (s, 1H); 6.89 (d, 1H); 6.57 (d, 1H); 4.08 (m, 1H); 3.71 (s, 3H); 2.18 (s, 3H); 1.61 (dd, 2H); 1.44 (dd, 2H); 1.05 (d, 12H).

EXAMPLE 9

(2Z,4E)-5-(5-Chlorobenzofuran-2-yl)-N-(3-diethylaminopropyl)-2-methoxy-2,4-pentadienamide. A solution of (2Z,4E)-5-(5-chlorobenzofuran-2-yl)-2-methoxy-2,4-pentadienoic acid (88 mg, 0.32 mmol), 3-dimethylamino propylamine (46 mg, 0.35 mmol), 1-hydroxy-7-azabenzotriazole hydrate (44 mg, 0.32 mmol) and 1-(3-dimethylaminopropyl)-3-ethylcarbodiimide hydrochloride (62 mg, 0.5 mmol) in DMF (2 ml) was stirred at RT for 6 hours. After the same work up as seen in example 3 pure title compound was obtained (60 mg, 0.153 mmol, yield 48.0%) as yellow crystals, mp.=150° dec.

$^1$H-DMSO-$d_6$): 8.42 (t, 1H); 7.70 (d, 1H); 7.63 (d, 1H); 7.34 (dd, 1H); 7.18 (dd, 1H); 6.99 (s, 1H); 6.91 (d, 1H); 6.66 (d, 1H); 3.73 (s, 3H); 3.25 (bq, 2H); 2.66 (bt, 6H); 1.68 (bt, 2H); 1.04 (t, 6H).

Preparation 8

Benzothiophen-2-carboxaldehyde. $LiAlH_4$ (7.6 g, 200 mmol) was suspended under stirring at 0° under Ar in anhydrous THF (400 ml), then N-methylpiperazine dihydrochloride (17.3 g, 100 mmol) was added portionwise in 10 min. N-methylpiperazine (30 g, 300 mmol) was then added dropwise, the mixture was warmed to RT and stirring continued for 2 hours. The surnatant of this suspension was then added by syringe to a stirred solution at 0° under Ar of benzothiophen-2-carboxylic acid (7.13 g, 40.0 mmol) in anhydrous THF (200 ml). The mixture was refluxed for 4 hours and after the same procedure as in preparation 6 pure title compound was obtained (4.6 g, 28.4 mmol, yield 70.9%) as dark orange crystals.

Preparation 9

(2E)-3-(Benzothiophen-2-yl)-2-propenal. A solution of benzothiophene-2-carboxaldehyde (3 g, 18.4 mmol) and formylmethylenetriphenylphosphorane (5.62 g, 18.4 mmol) in $CH_2Cl_2$ (100 ml) was treated as seen in preparation 1. After a chromatography on silicagel (n-heptane/EtOAc 4/1) pure title compound was obtained (1.00 g, 5.31 mmol, yield 28.9%) as yellow crystals, m.p.=88°.

EXAMPLE 10

Methyl (2Z,4E)-5-(benzothiophen-2-yl)-2-methoxy-2,4-pentadienoate. A suspension of methyl 2-methoxy-2-triphenylphosphonium acetate (4.72 g, 10.6 mmol) and DBU (1.62 g, 10.6 mmol) in $CH_2Cl_2$ (50 ml) was stirred at RT for 15 minutes. Then (2E)-3-(benzothiophen-2-yl)-2-propenal (1.0 g, 5.31 mmol) was added and the reaction conducted as seen for example 1. After a chromatography on silicagel (n-heptane/EtOAc 4/1) pure title compound was obtained (107 mg, 0.39 mmol, yield 7.3%) as yellow crystals.

$^1$H-DMSO-$d_6$): 7.66-7.81 (m, 3H); 7.27-7.34 (m, 2H); 7.20 (s, 1H); 6.87 (d, 1H); 6.05 (d, 1H); 3.91 (s, 3H); 3.75 (s, 3H).

EXAMPLE 11

(2Z,4E)-5-(Benzothiophen-2-yl)-2-methoxy-2,4-pentadienoic acid. To a stirred solution of methyl (2Z,4E)-5-(benzothiophen-2-yl)-2-methoxy-2,4-pentadienoate (107 mg, 0.39 mmol) in EtOH/water 1/1 (10 ml) potassium hydroxide (47 mg, 0.78 mmol) was added. The solution was refluxed for 1 hour, then it was treated as seen in example 2. Pure title compound (54 mg, 0.207 mmol, yield 53.2%) was obtained as yellow crystals.

$^1$H-NMR (DMSO-$d_6$): 7.89 (m, 1H); 7.76 (m, 1H); 7.62 (dd, 1H); 7.38 (s, 1H); 7.31-7.38 (m, 2H); 7.04 (d, 1H); 6.22 (d, 1H); 3.66 (s, 3H).

EXAMPLE 12

(2Z,4E)-5-(Benzothiophen-2-yl)-2-methoxy-N-[(1,2,2,6,6-pentamethyl)-piperidin-4-yl]-2,4-pentadienamide. A solution of (2Z,4E)-5-(benzothiophen-2-yl)-2-methoxy-2,4-pentadienoic acid (53 mg, 0.20 mmol), 4-amino-1,2,2,6,6-pentamethylpiperidine (34 mg, 0.20 mmol), 1-hydroxy-7-azabenzotriazole hydrate (27 mg, 0.20 mmol) and 1-(3-dimethylaminopropyl)-3-ethylcarbodiimide hydrochloride (38 mg, 0.20 mmol) in DMF (1 ml) was stirred at RT for 6 hours. After the same work up as seen in example 3 pure title compound was obtained (22 mg, 0.054 mmol, yield 26.6%) as white crystals, m.p.=240°.

$^1$H-NMR (DMSO-$d_6$): 7.73-7.94 (m, 4H); 7.33 (bs, 3H); 6.91 (d, 1H); 5.99 (d, 1H); 3.67 (s, 3H); 2.18 (s, 3H); 1.62 (bd, 2H); 1.42 (bt, 2H); 1.06 (d, 12H).

Preparation 10

(E)-3-(3-Methylbenzothiophen-2-yl)-2-propenal. 3-Methylbenzo[b]thiophene-2-carboxaldehyde (4.2 g, 23.8 mmol) was dissolved in dry toluene (100 ml) and treated with (formylmethylene)triphenylphosphorane (7.35 g, 24.2 mmol). The reaction mixture was heated to 80° C. for 10 hours, allowed to cool and the residue was washed with 200 ml of hexane/$Et_2O$ 1/1 and then triturated with isopropyl ether to give pure title compound (2.5 g, 12.38 mmol, yield 52.0%), m.p.=90–92+ C.

EXAMPLE 13

Methyl (2Z,4E)-2-(methoxy-5-(3-methylbenzothiophen-2-yl)-2,4-pentadienoate and methyl (2Z,4E)-2-(methoxy-5-(3-methylbenzothiophen-2-yl)-2,4-pentadienoate. A solution of (E)-3-[2-(3-methylbenzothiophen-2yl)]-2-propenal (1 g, 5 mmol) in $CH_2Cl_2$ (30 ml) under nitrogen was treated with methoxycarbonylmethyl-2-methoxy triphenylphosphonium bromide (4.45 g, 10 mmol) and DBU (1.5 ml, 10 mmol). The reaction mixture was stirred at room temperature for 2 hours, washed with 10% aqueous HCl (5 ml), saturated solution of $NaHCO_3$ (5 ml) and brine (5 ml), dried over $Na_2SO_4$ and evaporated under vacuum. The residue was purified by chromatography on silicagel (hexane/EtOAc 7/3) to afford, after trituration with isopropyl ether, methyl (2Z,4E)-2-methoxy-5-)3-methylbenzothiophen-2-yl)-2,4-pentiadienoate (380 mg, 1.32 mmol, yield 26.3%), m.p.=106–107° C., and methyl (2E,4E)-2-methoxy-5-(methylbenzothiophen-2-yl)-2,4-pentadienoate, (13 mg, 0.050 mmol, yield 1.0%), m.p.=91–92° C.

Methyl (2Z,4E)-2-methoxy-5-(3-methylbenzothiophen-2-yl)-2,4-pentadienoate: $^1$H-NMR (acetone-$d_6$): 7.84 (m, 1H); 7.75 (m, 1H); 7.45-7.35 (m, 3H); 7.00 (d, 1H); 6.92 (d, 1H); 3.80 (s, 6H); 2.48 (s, 3H).

Methyl (2Z,4E)-2-methoxy-5-(3-methylbenzothiophen-2-yl)-2,4-pentadienoate: $^1$H-NMR (acetone-$d_6$): 7.81 (m, 1H); 7.71 (dd, 1H); 7.69 (m, 1H); 7.40-7.31 (m, 2H); 7.18 (d, 1H); 6.32 (d, 1H); 3.82 (s, 3H); 3.72 (s, 3H); 2.44 (s, 3H).

Preparation 11

(2E)-3-(Quinolin-2yl)-prop-2-enal. A solution of quinolin-2-carboxaldehyde (3.5 g, 22.3 mmol) and formyl-methylenetriphenylphosphorane (6.79 g, 22.3 mmol) in $CH_2Cl_2$ (180 ml) was treated as seen in preparation 1. After a chromatography on silicagel (n-heptane/EtOAc 4/1) pure title compound was obtained (460 mg, 2.51 mmol, yield 11.3%) as grey needles, m.p.=85°.

EXAMPLE 14

Methyl (2Z,4E)-5-(quinolin-2-yl)-2-methoxy-2,4-pentadienoate. A suspension of methyl 2-methoxy-2-triphenylphosphonium acetate (2.22 g, 5.0 mmol) and DBU (750 mg, 5.0 mmol) in $CH_2Cl_2$ (20 ml) was stirred at RT for 15 minutes. Then (2E)-3-(quinolin-2-yl)-propenal (460 mg, 2.51 mmol) was added and the reaction conducted as seen for example 1. After a chromatography on silicagel (n-heptane/EtOAc 4/1) pure title compound was obtained (450 mg, 1.67 mmol, yield 66.6%) as brown crystals, m.p.=88°.

$^1$H-NMR (200 MHz, $d_6$DMSO): 8.36 (d, 1H); 7.99 (t, 2H); 7.72-7.84 (m, 3H), 7.60 (dd, 1H); 7.23 (d, 1H); 6.98 (d, 1H); 3.79 (s, 3H); 3.78 (s, 3H).

LIST OF ABBREVIATIONS USED IN THE ABOVE PREPARATIONS AND EXAMPLES

| | |
|---|---|
| Celite | Registered trade mark for dicalite |
| DMF | Dimethylformamide |
| EI | Electron Impact |
| AcOEt | Ethyl acetate |
| FAB POS | Fast Atom Bombardment/Positive ions detection |
| MS | Mass Spectrum |
| THF | Tetrahydrofuran |
| TSP | ThermoSpray |

Biological Assays

Background. It is known that, upon attachment to bone, an electrogenic $H^+$-adenosine triphosphatase (ATPase) is polarised to the osteoclast-bone interface. The pump transports massive quantities of protons into the resorption microenvironment to effect mobilisation of the bone mineral and to create the acidic pH required by collagenases to degrade the bone matrix.

The vacuolar nature of the osteoclast proton pump was originally recognised by Blair [H. C. Blair at al., Science, 245, 855 (1989)] and than confirmed by Bekker [P. J. Bekker et al., J. Bone Min. Res., 5, 569 (1990)] and Väänänen [K. K. Väänänen et al., J. Cell. Biol., 111, 1305 (1990)]. Evidence was based upon preparations of ruffled membrane fragments from avian osteoclasts (obtained from the medullar bone of calcium-starved egg-laying hens). The resulting membrane vesicles acidify in response to ATP, which is easily assessed by measuring the fluorescence quench of acridine orange, a weak base which accumulates into acidic compartments.

The biochemical pattern indicated that the osteoclast proton pump belonged to the vacuolar-like ATPases since proton transport was inhibited by N-ethylmaleimide (NEM), a sulphydryl reagent, and by bafilomycin $A_1$, a selective inhibitor of vacuolar $H^+$-ATPases [J. E. Bowman, et al., Proc. Natl. Acad. Sci. USA 85, 7972 (1988)], whilst it was not inhibited by ouabain, an inhibitor of $Na^+/K^+$-ATPases; sodium orthovanadate, an inhibitor of p-ATPases, or by omeprazole or SCH 28080, both of which are inhibitors of gastric $H^+/K^+$-ATPase [J. P. Mattson et al., Acta Physiol. Scand., 146, 253 (1992)].

It is known that specific inhibitors of vacuolar ATPases, such as bafilomycin $A_1$, are able to inhibit bone resorption in osteoclast cultures [K. Sundquist et al., Biochem. Biophys. Res. Commun. 168, 309–313 (1990)].

Inhibition of v-ATPase Proton Transport in Membrane Vesicles

Preparation of crude bone microsomes from calcium-starved egg-laying hens.

Vesicles were prepared from medullar bone obtained from tibiae and femurs of egg-laying hens which were calcium-starved for at least 15 days. Briefly, bone fragments were scraped with a 24 scalpel blade, suspended in 40 ml of isolation medium (0.2M sucrose, 50 mM KCl, 10 mM Hepes, 1 mM EGTA, 2 mM dithiotheitrol, pH 7.4) and filtered through a 100 μm pore size nylon mesh. The whole procedure was performed at 4° C. After homogenisation in a potter (20 strokes) in 40 ml of isolation medium an initial centrifugation ($6,500 \times g_{max} \times 20$ min) was performed to remove mitochondria and lysosomes. The supernatant was centrifuged at $100,000 \times g_{max}$ for 1 hr and the pellet was collected in 1 ml of isolation medium, divided into 200 μl aliquots, immediately frozen in liquid nitrogen and stored at 31 80° C. The protein content was determined using a Biorad colourimetric kit according to Bradford [M. Bradford, Anal. Biochem., 72, 248 (1976)]. For the proton transport assay, 5–10 μl of membranes were used.

Purification of osteoclast membranes. 1 ml of crude microsomal vesicles prepared above were applied (about 0.2 ml per tube) on the top of a sucrose step-gradient consisting of 3.5 ml of 15%, 30% and 45% (w/w) sucrose in isolation medium and centrifuged at 280,000 $g_{max}$ for 2 hours (SW 41 Ti rotor). After centrifugation the 30–45% sucrose interfaces were collected, diluted approx. 20-fold in isolation medium and pelletted at 100,000 $g_{max}$ for 1 hour (SW 28 rotor). The pellet was then resuspended in 1 ml of isolation medium, aliquoted and frozen in liquid $N_2$ and stored at −80° C. until used.

Proton transport in membrane vesicles was assessed, semi-quantitatively, by measuring the initial slope of flourescence quench of acridine orange (excitation 490 nm; emission 530) after addition of 5–20 μl of membrane vesicles in 1 ml of buffer containing 0.2M sucrose, 50 mM KCl, 10 mM Hepes pH 7.4, 1 mM $ATP.Na_2$, 1 mM CDTA, 5 μM valinomycin and 4 μM acridine orange. The reaction was started by addition of 5 mM $MgSO_4$. Results were expressed as the percent of the mean of two controls.

Inhibition of bafilomycin-sensitive ATPase activity was assessed in purified membrane vesicles by measuring the release of inorganic phosphate (Pi) during 30 min of incubation at 37° C. in a 96-well plate either in the presence or in the absence of bafilomycin A1. The reaction medium contained 1 mM ATP, 10 mM HEPES-Tris pH 8, 50 MM KCl, 5 uM valinomycin, 5 uM nigericin, 1 mM CDTA-Tris, 100 uM ammonium molybdate, 0.2M sucrose and membranes (20 ug protein/ml). The reaction was initiated by $MgSO_4$ (8-arm pipette) and stopped, after 30 min, by addition of 4 volumes of the malachite green reagent (96-arm pipette) prepared according to Chan [Anal. Biochem. 157, 375 (1986)]. Absorbance at 650 nm was measured after 2 min using a microplate reader. Results are expressed as $\mu mol\ (Pi) \times mg\ protein^{-1} \times hour^{-1}$ and, for each experiment, represent the mean±sem of triplicates.

PHARMACOLOGICAL DATA

Inhibition of Bafilomycin-Sensitive ATPase in Chicken Osteoclasts

| Ex. No | $IC_{50}$ (μM) ATPase assay |
|---|---|
| 3 | 8.6 |
| 5 | 11 |
| 8 | 0.5 |
| 9 | 10 |
| 12 | 10.6 |

Inhibition of Bone Resorption

In Vitro assays

1) Bone resorption can be assessed as described previously in the literature [T. J. Chambers et al., Endocrinology, 1985, 116, 234]. Briefly, osteoclasts were mechanically disaggregated from neonatal rat long bones into Hepes-buffered medium 199 (Flow, UK). The suspension was agitated with a pipette, and the larger fragments were allowed to settle for 30 sec. The cells were then added to two wells of a multiwell dish containing bone slices (each measuring 12 mm²). After 15 min at 37° C. the bone slices were removed, washed in medium 199 and placed in individual wells of a 96-well plate. These were incubated for 24 hrs in a total volume of 2 ml of culture medium, consisting of 10% foetal calf serum in Hanks-buffered MEM, in the presence or absence of drug. The number of osteoclasts and bone resorption were quantified by confocal laser scanning microscopy (CLSM): the bone slices were fixed with 2% glutaraldehyde in 0.2M cacodylate buffer and the osteoclasts on each bone slice were stained for tartrate-resistant acid phosphatase. After counting the number of large, multinucleated, red-stained cells, the bone slices were immersed in 10% sodium hypochlorite for 60 min to remove cells, washed in distilled water and sputter-coated with gold. The entire surface of each bone slice was then examined in CLSM. The number and the size of the osteoclastic excavations, the plain area and the volume of bone resorbed was recorded. Results were expressed as mean pit number per osteoclast, mean area per osteoclast or mean volume per osteoclast.

2) Inhibition of PTH-stimulated $^{45}Ca^{2+}$ release from pre-labelled foetal rat long bone. The assay is based on that described by Raisz (*J. Clin. Invest.* 44:103–116, 1965). Time-mated Sprague-Dawley rats were injected subcutaneously with 200 mCi of $^{45}CaCl2$ on the 18th day of gestation. On the following day, the foetuses were removed aseptically and the radii and ulnae were dissected free of adjacent soft tissue and the cartilaginous ends, and then cultured for 24 hr at 37° C. in BGJ medium containing 1 mg/ml BSA. The bones were then transferred to fresh medium containing the test compounds (0.1–50 μM) with and without PTH (12 nM) and were incubated for an additional 48 hr. The media were collected and the bones extracted to determine the mean % calcium release by scintillation counting. Results were expressed as the % inhibition compared to the amount of calcium released from cultures incubated with PTH alone.

In vivo assays

Prevention of retinoid-induced hypercalcaemia. The method used was that described by Trechsel et al., (*J. Clin. Invest.* 80:1679–1686, 1987). Briefly, male Sprague-Dawley rats weighting 160–200 g (10 per group) were thyroparathyroidectomised and were treated subcutaneously with the retinoid Ro 13-6298 (30 μg/day) for three days and this was found to significantly increase blood serum calcium by 4–5 mg/100 ml. For inhibition of this effect, rats were treated simultaneously with test compounds i.v. or p.o. at 0.1–100 mg/kg, or vehicle and blood calcium was measured as described above, before treatment and one day after the last administration. Results were expressed as % inhibition with respect to vehicle-treated animals.

Prevention of bone loss in osteoporosis induced by ovariectomy and immobilisation. Seven groups of 10 Sprague-Dawley rats (200 g) underwent ovariectomy plus neurectomy of the sciatic nerve in the right hind limb, while one group was sham-operated according to the method described by Hayashi et al., (*Bone* 10:25–28, 1989). It was demonstrated that a steady-state was attained in the amount of trabecular bone lost 6–12 weeks after the operations. During a 6-week period, the operated animals received the test compounds (0.1–100 mg/kg p.o. u.i.d.), or vehicle. At the end of this treatment period, the animals were sacrificed and the tibia and femur of the hind limb removed. The tibia wet and dry weight were determined, and the density (displacement of water) and ashes content (total weight, calcium and phosphorous content) also measured. The femur fixed in 10% formalin, de-mineralised in 5% formic acid and the coronal midshaft and longitudinal section of the distal metaphysis cut and stained with haematoxilin and eosin. Histomorphometric evaluation was made using a semi-automated image analyser (Immagini & Computer, Milan, Italy). In the distal metaphysis, the % trabecular bone area in the secondary spongiosa (which is the trabecular bone 1 mm from the epiphyseal growth plate to about 4 mm towards the midshaft giving a total area of 5 mm$^2$) and the number of trabeculae (according to Parfitt et al., *J. Bone Min. Res.* 2:595, (1987)) were determined in all animals. In the midshaft, the medullary, cortical (CA) and total (TA) cross-sectional area was measured and the cortical index (CI) determined from the formula CI=CA/TA.

Prevention of bone loss in ovariectomised mature rats. The methodology employed is based on that described by Wronsky et al. [*J. Bone Min. Res.*, 6, 387 (1991)]. The bone loss, prevalently cancellous, occuring after the surgery is monitored by dual emission X-ray absorptiometry (DEXA) measurements of bone mineral density (BMD) of long bones and by HPLC measurements of urinary levels of products of bone collagen breakdown, such as the cross-link residues pyridinoline (PYD), deoxypyridinoline (DPD) and lysine glycosides, i.e. galactosyl-hydroxylysine (GHYL) and glucosyl-galactosyl-hydroxylysine (GGHYL).

Groups of 7–10 female Sprague-Dawley rats, about 90 days old and weighing 200–250 g are used. Rats are anesthetised by sodium pentobarbital (35 mg/kg i.v.), laparotomy is performed and ovaries are bilaterally removed. Wounds are adequately disinfected and sutured. A group is sham operated. During a 4-week experimental period, the operated animals receive test compounds in the appropiate vehicle (0.1–100 mg/kg p.o. u.i.d.) or vehicle alone.

Twenty-four-hr urine samples are collected for PYD, DPD, GHYL and GGHYL determinations before and 2, 4, 8, 11, 15, 18, 22 and 25 days after surgery. The aliquots of urine are frozen and stored at −20° C. until HPLC analysis.

Before and at the end of the experimental period, the bone metaphyseal mineral densities of left distal femur and proximal tibia were evaluated in vivo using lightly anaesthetised animals. Results are expressed as % of prevention versus vehicle treated animals.

Other Therapeutic Utilities

The activity of the compounds of the invention for the other utilities mentioned herein may be determined by according to the following methods which are incorporated herein:

1. Antitumor activity may be determined according to the methods disclosed in published International Application, Publication number 93/18652; in particular the screen employed, experimental details and bibliography of M. R. Boyd et al., *Status of the NCI preclinical antitumor drug discovery screen; principles and practices of Oncology,* 3, issue 10, Oct. 1989, Lippincott.

2. Antiviral activity may be assessed using the in vitro assays reported by H. Ochiai et al., *Antiviral Research,* 27, 425–430 (1995) or by C. Serra et al., *Pharmacol. Res.,* 29, 359 (1994). Anti-HIV activity can be assessed as reported in the literature, for example by S. Velásquez et al., *J. Med. Chem.,* 38, 1641–1649 (1995).

3. Antiulcer activity may be assessed in vivo using the methods reported in the literature, for example, as described by C. J. Pfeiffer, *Peptic Ulcer,* C. J. Pfeiffer Ed., Munksgaard Publ., Copenaghen, 1971. In vitro assays for inhibition of vacuolization induced by *Helicobacter pylori* are described, for example, by E. Papini et al., *FEMS Microbiol. Lett.,* 113, 155–160 (1993)

4. Usefulness in treating Alzheimer's disease may be determined using models in vitro such as inhibition of amiloyd-β production as described in the literature by J. Knops et al., *J. Biol. Chem.*, 270, 2419–2422 (1995) or by models in vivo: such as the transgenic mouse model overexpressing human APP reported by D. Games et al., *Nature*, 373, 523–527 (1995).

5. Immunosuppressant activity can be assessed as reported in the literature, for example by M. -K. Hu et al., *J. Med. Chem.*, 38, 4164–4170 (1995)

6. Antilipidemic activity can be assessed as reported in the literature, for example by E. A. L. Biessen et al., *J. Med. Chem.*, 38, 1846–1852 (1995). Antiatherosclerotic activity may be assessed by using animal models of atherosclerosis, such as the atherosclerotic rabbit model, which are reported in the literature, for example by R. J. Lee et al., *J. Pharm. Exp. Ther.*, 184, 105–112 (1973).

7. Angiostatic activity may be assessed using the methods reported in the literature, for example as described by T. Ishii et al., *J. Antibiol.*, 48, 12 (1995).

We claim:

1. A compound of formula (I):

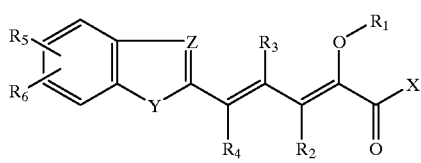

(I)

or a salt thereof, or a solvate thereof, wherein:

$R_1$ represents an alkyl group or a substituted or unsubstituted aryl group;

$R_2$, $R_3$ and $R_4$ each independently represent hydrogen, alkyl, aryl or substituted aryl;

$R_5$ and $R_6$ each independently represents hydrogen, hydroxy, amino, alkoxy, optionally substituted aryloxy, optionally substituted benzyloxy, alkylamino, dialkylamino, halo, trifluoromethyl, trifluoromethoxy, nitro, alkyl, carboxy, carbalkoxy, carbamoyl, alkylcarbamoyl, or $R_5$ and $R_6$ together represent methylenedioxy, carbonyldioxy or carbonyldiamino;

X represents a hydroxy or an alkoxy group wherein the alkyl group may be substituted or unsubstituted or X represents a group $NR_SR_t$ wherein $R_S$ and $R_t$ each independently represent hydrogen, alkyl, substituted alkyl, optionally substituted alkenyl, optionally substituted aryl, optionally substituted arylalkyl, an optionally substituted heterocyclic group or an optionally substituted heterocyclyalkyl group, or $R_S$ and $R_t$ together with the nitrogen to which they are attached form a heterocyclic group; and Y represents O or S and Z represents CH, CH=CH or N; or Y represents $NR_7$ wherein $R_7$ represents hydrogen, hydroxy, alkanoyl, alkyl, aminoalkyl, hydroxyalkyl, carboxyalkyl, carbalkoxyalkyl, carbamoyl or aminosulphonyl and Z represents CH=CH or N.

2. A compound according to claim 1, wherein Y represents O or S and Z represents CH, CH=CH or N.

3. A compound according to claim 1, wherein Z represents CH or CH=CH.

4. A compound according to claim 1, wherein $R_1$ represents methyl.

5. A compound according to claim 1, wherein $R_2$, $R_3$ and $R_4$ each independently represent hydrogen.

6. A compound according to claim 1, wherein X represents N $R_S$ $R_t$, wherein $R_t$ is hydrogen and $R_S$ represents a group of formula (H1):

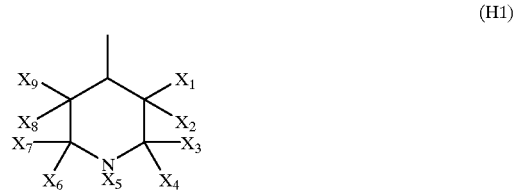

(H1)

wherein $X_1$, $X_2$, $X_3$, $X_4$, $X_5$, $X_6$, $X_7$ and $X_8$ are each independently selected from hydrogen, hydroxy, ($C_1$–$C_6$), alkyl cycloalkyl (spirocondensed), mono or poly hydroxyalkyl, alkoxyalkyl, hydroxy-alkoxyalkyl, alkanoyl, alkoxycarbonyl, aminoalkyl (optionally alkylated or acylated at nitrogen);

or one of $X_4$ with $X_6$ and $X_2$ with $X_8$ represents a $C_{2-4}$ alkylene chain and the remaining variables $X_1$, $X_3$, $X_7$ and $X_7$ each independently represent hydrogen, hydroxy, lower alkyl ($C_1$–$C_6$), cycloaklyl (spirocondensed), mono or poly hydroxyalkyl, alkoxyalkyl, hydroxyalkoxyalkyl, alkanoyl, alkoxycarbonyl, aminoalkyl (optionally alkylated or acylated at nitrogen); and $X_5$ represents hydrogen or lower alkyl, mono or polyhydroxyalkyl, mono or diaminoalkyl, aminocarbonyl, alkyl, carboxyalkyl, carbalkoxyalkyl, aryl, heterocyclyl, acyl, carbamoyl, alkylamino(cyanimidoyl), aminoalkanoyl, hydroxyalkanoyl.

7. A process for the preparation of a compound of formula (I) or a salt thereof or a solvate thereof, which process comprises reacting a compound of formula (II):

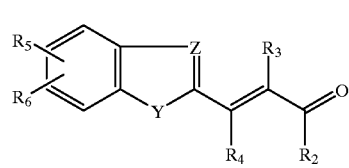

(II)

wherein $R_2$, $R_3$, $R_4$, $R_5$, $R_6$, Y and Z are defined in relation to formula (I), with a reagent capable of converting a moiety of formula

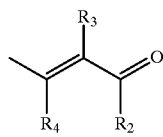

into a moiety of formula (a):

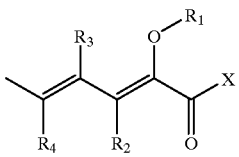

wherein $R_1$, $R_2$, $R_3$, $R_4$ and X are as defined in relation to formula (I); and thereafter, as necessary, carrying out one or more of the following reactions:

(i) converting one compound of formula (I) into another compound of formula (I);

(ii) removing any protecting group;

(iii) preparing a salt or a solvate of the compound so formed.

8. A pharmaceutical composition comprising a compound of formula (I) as defined in claim 1, or a pharmaceutically acceptable salt thereof or a pharmaceutically acceptable solvate thereof, and a pharmaceutically acceptable carrier therefor.

9. A compound of formula (I) according to claim 1, or a pharmaceutically acceptable salt thereof, or a pharmaceutically acceptable solvate thereof, for use as an active therapeutic substance.

10. A method for the treatment and/or prophylaxis of diseases associated with over activity of osteoclasts in mammals which method comprises the administration of an effective non-toxic amount of a compound of formula (I) according to claim 1, or a pharmaceutically acceptable salt thereof, or a pharmaceutically acceptable solvate thereof.

\* \* \* \* \*